US009675671B2

(12) United States Patent
McTavish

(10) Patent No.: US 9,675,671 B2
(45) Date of Patent: Jun. 13, 2017

(54) FUSION PROTEINS CONTAINING INSULIN-LIKE GROWTH FACTOR-1 AND EPIDERMAL GROWTH FACTOR AND VARIANTS THEREOF AND USES THEREOF

(71) Applicant: Hugh McTavish, Pine Springs, MN (US)

(72) Inventor: Hugh McTavish, Pine Springs, MN (US)

(73) Assignee: IGF Oncology, LLC, Pine Springs, MN (US)

( * ) Notice: Subject to any disclaimer, the term of this patent is extended or adjusted under 35 U.S.C. 154(b) by 0 days.

(21) Appl. No.: 14/594,980

(22) Filed: Jan. 12, 2015

(65) Prior Publication Data

US 2015/0196656 A1 Jul. 16, 2015

Related U.S. Application Data

(60) Provisional application No. 61/926,386, filed on Jan. 12, 2014.

(51) Int. Cl.

| C07K 14/52 | (2006.01) |
|---|---|
| C07K 14/525 | (2006.01) |
| C07K 14/485 | (2006.01) |
| C07K 14/495 | (2006.01) |
| A61K 38/19 | (2006.01) |
| A61K 31/519 | (2006.01) |
| A61K 31/4184 | (2006.01) |
| A61K 47/48 | (2006.01) |
| A61K 51/08 | (2006.01) |
| C07K 14/65 | (2006.01) |
| A61K 31/196 | (2006.01) |
| A61K 38/00 | (2006.01) |

(52) U.S. Cl.
CPC .......... *A61K 38/191* (2013.01); *A61K 31/196* (2013.01); *A61K 31/4184* (2013.01); *A61K 31/519* (2013.01); *A61K 47/48269* (2013.01); *A61K 51/08* (2013.01); *C07K 14/485* (2013.01); *C07K 14/495* (2013.01); *C07K 14/52* (2013.01); *C07K 14/525* (2013.01); *C07K 14/65* (2013.01); *A61K 38/00* (2013.01); *C07K 2319/02* (2013.01); *C07K 2319/21* (2013.01)

(58) Field of Classification Search
None
See application file for complete search history.

(56) References Cited

U.S. PATENT DOCUMENTS

| 4,876,242 A | 10/1989 | Applebaum |
|---|---|---|
| 4,975,278 A | 12/1990 | Senter |
| 5,122,368 A | 6/1992 | Greenfield |
| 5,444,045 A | 8/1995 | Francis |
| 5,518,888 A | 5/1996 | Waldman |
| 5,830,995 A * | 11/1998 | Shoyab et al. ............... 530/322 |
| 5,869,045 A | 2/1999 | Hellstrom |
| 5,886,141 A * | 3/1999 | Folkman et al. ............. 530/300 |
| 7,811,982 B2 | 10/2010 | McTavish |
| 8,017,102 B2 * | 9/2011 | McTavish .................... 424/1.69 |
| 2002/0197261 A1 | 12/2002 | Li |
| 2003/0092631 A1 | 5/2003 | Deshayes |
| 2003/0138430 A1 | 7/2003 | Stimmel |
| 2003/0180937 A1* | 9/2003 | Georgiou ............ C12N 15/625 506/10 |
| 2004/0023887 A1 | 2/2004 | Pillutla |
| 2004/0038303 A1 | 2/2004 | Unger |
| 2004/0086503 A1 | 5/2004 | Cohen |
| 2004/0137071 A1 | 7/2004 | Unger |
| 2004/0142381 A1 | 7/2004 | Hubbard |
| 2011/0275566 A1* | 11/2011 | Besner ................ A61K 38/177 514/9.6 |

FOREIGN PATENT DOCUMENTS

| EP | 0309050 | 3/1989 |
|---|---|---|
| EP | 0398305 | 11/1990 |
| WO | WO 88/08715 | 11/1988 |
| WO | WO 93/21939 | 11/1993 |
| WO | WO 01/93900 | 12/2001 |
| WO | WO 02/49672 | 6/2002 |
| WO | WO 03/074551 | 9/2003 |

OTHER PUBLICATIONS

A Dictionary of Genetics (7 ed.), King et al. (eds), Oxford University Press, 2007, on-line entry for leader sequence peptide.2015. Website http://www.oxfordreference.com accessed Nov. 13, 2015.*
Molhoj et al., Nature Biotechnology, 22(12): 1502, Dec. 2014.*
Ayre SG, Garcia y Bellon DP, Garcia DP Jr. 2000. Insulin, chemotherapy, and the mechanisms of malignancy: the design and the demise of cancer, *Medical Hypotheses* 55:330-334.
Abita JP, Gauville C, Balitrand N, Gespach C, Canivet J. 1984. Binding of 125I-insulin to the human histiocytic lymphoma cell line U-937: effect of differentiation with retinoic acid. *Leuk Res.* 8(2):213-21.
Alabaster O, Vonderhaar BK, Shafie SM. 1981. Metabolic modification by insulin enhances methotrexate cytotoxicity in MCF-7 human breast cancer cells. *Eur J Cancer Clin Oncol.* 17(11):1223-8.
Schilsky RL, Bailey BD, Chabner BA. 1981. Characteristics of membrane transport of methotrexate by cultured human breast cancer cells. *Biochem Pharmacol.* 30(12):1537-42.
McTavish et al. 2009. Novel insulin-like growth factor-methotrexate covalent conjugate inhibits tumor growth in vivo at lower dosage than methotrexate alone. *Translational Research* 153:275-282.
Daughaday WH, Rotwein P. 1989. Insulin-like growth factors I and II. Peptide, messenger ribonucleic acid and gene structures, serum, and tissue concentrations. *Endocr Rev.* 10(1):68-91.
Stewart CE, Rotwein P. 1996. Growth, differentiation, and survival: multiple physiological functions for insulin-like growth factors. *Physiol Rev.* Oct. 1996;76(4):1005-26.
Yakar S, Wu Y, Setser J, Rosen CJ. 2002. The role of circulating IGF-I: lessons from human and animal models. *Endocrine.* 19(3):239-48.

(Continued)

*Primary Examiner* — Marianne P Allen
(74) *Attorney, Agent, or Firm* — Hugh McTavish

(57) ABSTRACT

Fusion proteins comprising cytokines, particularly insulin-like growth factor-1 (IGF-1) and variants thereof, epidermal growth factor (EGF), and other ligands to the EGF receptor, are provided. The fusion proteins further comprise SEQ ID NO:1 or other segments having lysine, glutamic acid, or aspartic acid residues. Uses for the fusion proteins are also provided.

11 Claims, 7 Drawing Sheets

(56) References Cited

OTHER PUBLICATIONS

Shackney SE, McCormack GW, Cuchural GJ Jr. 1978. Growth rate patterns of solid tumors and their relation to responsiveness to therapy: an analytical review. *Ann. Intern. Med.* 89:107-21.

Poznansky MJ, Singh R, Singh B, Fantus G. 1984. Insulin: carrier potential for enzyme and drug therapy. *Science* 223(4642):1304-6.

Bures L, Bostik J, Motycka K, Spundova M, Rehak L. 1988. The use of protein as a carrier of methotrexate for experimental cancer chemotherapy. III. Human serum albumin-methotrexate derivative, its preparation and basic testing. *Neoplasma* 35:329-42.

Ciftci K, Su J, Trovitch PB. 2003. Growth factors and chemotherapeutic modulation of breast cancer cells. *J Pharm Pharmacol* 55(8):1135-41.

Francis GL, Ross M, Ballard FJ, Milner SJ, Senn C, McNeil KA, Wallace JC, King R, Wells Jr. 1992. Novel recombinant fusion protein analogues of insulin-like growth factor (IGF)-I indicate the relative importance of IGF-binding protein and receptor binding for enhanced biological potency. *J Mol Endocrinol.* 8(3):213-23.

Tomas FM, Knowles SE, Chandler CS, Francis GL, Owens PC, Ballard FJ. 1993. Anabolic effects of insulin-like growth factor-I (IGF-I) and an IGF-I variant in normal female rats. *J Endocrinol.* 137(3):413-21.

Stehle G, Sinn H, Wunder A, Schrenk HH, Schutt S, Maier-Borst W, Heene DL. 1997. The loading rate determines tumor targeting properties of methotrexate-albumin conjugates in rats. *Anticancer Drugs* 8(7):677-85.

Grothey, A. et al. 1999. The role of unsulin-like growth factor I and its receptor in cell growth, transformation, apoptosis, and chemoresistance in solid tumors. *J. Cancer Res. Clin. Oncol.* 125:166-173.

Carlsson et al.. 1978. Biochem J. 173:723-727.

Laajoki et al. 2000. J. Biol. Chem. 275:1009-15.

Laajoki et al. 1997. FEBS Lett. 420:97-102.

Allen et al. Ligand-targeted therapeutics in anticancer therapy. 2002. Nature Reviews Cancer 2:750-763.

Wang et al. 2002. Insulin-like growth factor receptor-1 as an anti-cancer target: blocking transformation and inducing apoptosis. *Current Cancer Drug Targets* 2:191-207.

Bohula et al. 2003. Targeting the type-1 insulin-like growth factor receptor as anti-cancer treatment. *Anti-cancer Drugs* 14:669-682.

Akhlynina et al. 1997. J. Biol. Chem. 272:20328-31.

Leckett et al. 1992. Cytotechnology 10:125-136.

Satyamoorthy, K. et al. 2001. Insulin-like growth factor-1 induces survival and growth of biologically early melanoma cells . . . *Cancer Res.* 61:7138.

\* cited by examiner

SEQUENCE LISTING

<160> NUMBER OF SEQ ID NOS: 18

<210> SEQ ID NO 1
<211> LENGTH: 18
<212> TYPE: PRT
<213> ORGANISM: Artificial
<220> FEATURE:
<223> OTHER INFORMATION: Synthesized

<400> SEQUENCE: 1

Met Val Lys Gly Lys His His His His His Asn Gly Lys Gly Lys
1               5                   10                  15

Ser Lys

<210> SEQ ID NO 2
<211> LENGTH: 88
<212> TYPE: PRT
<213> ORGANISM: Artificial
<220> FEATURE:
<223> OTHER INFORMATION: Synthesized

<400> SEQUENCE: 2

Met Val Lys Gly Lys His His His His His Asn Gly Lys Gly Lys
1               5                   10                  15

Ser Lys Gly Pro Arg Thr Leu Cys Gly Ala Glu Leu Val Asp Ala Leu
            20                  25                  30

Gln Phe Val Cys Gly Asp Arg Gly Phe Tyr Phe Asn Lys Pro Thr Gly
        35                  40                  45

Tyr Gly Ser Ser Ser Arg Arg Ala Pro Gln Thr Gly Ile Val Asp Glu
    50                  55                  60

Cys Cys Phe Arg Ser Cys Asp Leu Arg Arg Leu Glu Met Tyr Cys Ala
65                  70                  75                  80

Pro Leu Lys Pro Ala Lys Ser Ala
                85

<210> SEQ ID NO 3
<211> LENGTH: 70
<212> TYPE: PRT
<213> ORGANISM: Homo sapiens

<400> SEQUENCE: 3

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu

Lys Pro Ala Lys Ser Ala
65                  70

<210> SEQ ID NO 4
<211> LENGTH: 71
<212> TYPE: PRT
<213> ORGANISM: Artificial
<220> FEATURE:
<223> OTHER INFORMATION: Synthesized

<400> SEQUENCE: 4

Phe Val Asn Gln His Leu Cys Gly Ser His Leu Val Glu Ala Leu Tyr
1               5                   10                  15

Leu Val Cys Gly Asp Arg Gly Phe Tyr Phe Asn Lys Pro Thr Gly Tyr
                20                  25                  30

Gly Ser Ser Ser Arg Arg Ala Pro Gln Thr Gly Ile Val Asp Glu Cys
            35                  40                  45

Cys Phe Arg Ser Cys Asp Leu Arg Arg Leu Glu Met Tyr Cys Ala Pro
        50                  55                  60

Leu Lys Pro Ala Lys Ser Ala
65                  70

<210> SEQ ID NO 5
<211> LENGTH: 83
<212> TYPE: PRT
<213> ORGANISM: Artificial
<220> FEATURE:
<223> OTHER INFORMATION: Synthesized

<400> SEQUENCE: 5

Met Phe Pro Ala Met Pro Leu Ser Ser Leu Phe Val Asn Gly Pro Arg
1               5                   10                  15

Thr Leu Cys Gly Ala Leu Val Asp Ala Leu Gln Phe Val Cys Gly Asp
                20                  25                  30

Arg Gly Phe Tyr Phe Asn Lys Pro Thr Gly Tyr Gly Ser Ser Ser Arg
            35                  40                  45

Arg Ala Pro Gln Thr Gly Ile Val Asp Glu Cys Cys Phe Arg Ser Cys
        50                  55                  60

Asp Leu Arg Arg Leu Glu Met Tyr Cys Ala Pro Leu Lys Pro Ala Lys
65                  70                  75                  80

Ser Glu Ala

<210> SEQ ID NO 6
<211> LENGTH: 70
<212> TYPE: PRT
<213> ORGANISM: Artificial
<220> FEATURE:
<223> OTHER INFORMATION: Synthesized

<400> SEQUENCE: 6

Gly Pro Arg Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
        50                  55                  60

```
Lys Pro Ala Lys Ser Ala
 65                  70
```

<210> SEQ ID NO 7
<211> LENGTH: 67
<212> TYPE: PRT
<213> ORGANISM: Artificial
<220> FEATURE:
<223> OTHER INFORMATION: Synthesized

<400> SEQUENCE: 7

```
Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
             20                  25                  30

Arg Arg Ala Pro Gln Thr Gly Ile Val Asp Glu Cys Cys Phe Arg Ser
         35                  40                  45

Cys Asp Leu Arg Arg Leu Glu Met Tyr Cys Ala Pro Leu Lys Pro Ala
     50                  55                  60

Lys Ser Ala
 65
```

<210> SEQ ID NO 8
<211> LENGTH: 71
<212> TYPE: PRT
<213> ORGANISM: Artificial
<220> FEATURE:
<223> OTHER INFORMATION: Synthesized

<400> SEQUENCE: 8

```
Met Val Lys Gly Lys His His His His His Asn Gly Lys Gly Lys
 1               5                  10                  15

Ser Lys Asn Ser Asp Ser Glu Cys Pro Leu Ser His Asp Gly Tyr Cys
             20                  25                  30

Leu His Asp Gly Val Cys Met Tyr Ile Glu Ala Leu Asp Lys Tyr Ala
         35                  40                  45

Cys Asn Cys Val Val Gly Tyr Ile Gly Glu Arg Cys Gln Tyr Arg Asp
     50                  55                  60

Leu Lys Trp Trp Glu Leu Arg
 65                  70
```

<210> SEQ ID NO 9
<211> LENGTH: 54
<212> TYPE: PRT
<213> ORGANISM: Artificial
<220> FEATURE:
<223> OTHER INFORMATION: Synthesized

<400> SEQUENCE: 9

```
Met Asn Ser Asp Ser Glu Cys Pro Leu Ser His Asp Gly Tyr Cys Leu
 1               5                  10                  15

His Asp Gly Val Cys Met Tyr Ile Glu Ala Leu Asp Lys Tyr Ala Cys
             20                  25                  30

Asn Cys Val Val Gly Tyr Ile Gly Glu Arg Cys Gln Tyr Arg Asp Leu
         35                  40                  45

Lys Trp Trp Glu Leu Arg
     50
```

<210> SEQ ID NO 10
<211> LENGTH: 160
<212> TYPE: PRT

-continued

<213> ORGANISM: Homo sapiens

<400> SEQUENCE: 10

Met Val Pro Ser Ala Gly Gln Leu Ala Leu Phe Ala Leu Gly Ile Val
1               5                   10                  15

Leu Ala Ala Cys Gln Ala Leu Glu Asn Ser Thr Ser Pro Leu Ser Ala
                20                  25                  30

Asp Pro Pro Val Ala Ala Val Val Ser His Phe Asn Asp Cys Pro
            35                  40                  45

Asp Ser His Thr Gln Phe Cys Phe His Gly Thr Cys Arg Phe Leu Val
    50                  55                  60

Gln Glu Asp Lys Pro Ala Cys Val Cys His Ser Gly Tyr Val Gly Ala
65                  70                  75                  80

Arg Cys Glu His Ala Asp Leu Leu Ala Val Val Ala Ala Ser Gln Lys
                85                  90                  95

Lys Gln Ala Ile Thr Ala Leu Val Val Val Ser Ile Val Ala Leu Ala
                100                 105                 110

Val Leu Ile Ile Thr Cys Val Leu Ile His Cys Cys Gln Val Arg Lys
            115                 120                 125

His Cys Glu Trp Cys Arg Ala Leu Ile Cys Arg His Glu Lys Pro Ser
    130                 135                 140

Ala Leu Leu Lys Gly Arg Thr Ala Cys Cys His Ser Glu Thr Val Val
145                 150                 155                 160

<210> SEQ ID NO 11
<211> LENGTH: 252
<212> TYPE: PRT
<213> ORGANISM: Homo sapiens

<400> SEQUENCE: 11

Met Arg Ala Pro Leu Leu Pro Pro Ala Pro Val Val Leu Ser Leu Leu
1               5                   10                  15

Ile Leu Gly Ser Gly His Tyr Ala Ala Gly Leu Asp Leu Asn Asp Thr
                20                  25                  30

Tyr Ser Gly Lys Arg Glu Pro Phe Ser Gly Asp His Ser Ala Asp Gly
            35                  40                  45

Phe Glu Val Thr Ser Arg Ser Glu Met Ser Ser Gly Ser Glu Ile Ser
    50                  55                  60

Pro Val Ser Glu Met Pro Ser Ser Glu Pro Ser Ser Gly Ala Asp
65                  70                  75                  80

Tyr Asp Tyr Ser Glu Glu Tyr Asp Asn Glu Pro Gln Ile Pro Gly Tyr
                85                  90                  95

Ile Val Asp Asp Ser Val Arg Val Glu Gln Val Val Lys Pro Pro Gln
            100                 105                 110

Asn Lys Thr Glu Ser Glu Asn Thr Ser Asp Lys Pro Lys Arg Lys Lys
    115                 120                 125

Lys Gly Gly Lys Asn Gly Lys Asn Arg Arg Asn Arg Lys Lys Lys Asn
130                 135                 140

Pro Cys Asn Ala Glu Phe Gln Asn Phe Cys Ile His Gly Glu Cys Lys
145                 150                 155                 160

Tyr Ile Glu His Leu Glu Ala Val Thr Cys Lys Cys Gln Gln Glu Tyr
                165                 170                 175

Phe Gly Glu Arg Cys Gly Glu Lys Ser Met Lys Thr His Ser Met Ile
            180                 185                 190

Asp Ser Ser Leu Ser Lys Ile Ala Leu Ala Ala Ile Ala Ala Phe Met

```
            195                 200                 205
Ser Ala Val Ile Leu Thr Ala Val Ala Val Ile Thr Val Gln Leu Arg
    210                 215                 220

Arg Gln Tyr Val Arg Lys Tyr Glu Gly Glu Ala Glu Arg Lys Lys
225                 230                 235                 240

Leu Arg Gln Glu Asn Gly Asn Val His Ala Ile Ala
                245                 250

<210> SEQ ID NO 12
<211> LENGTH: 208
<212> TYPE: PRT
<213> ORGANISM: Homo sapiens

<400> SEQUENCE: 12

Met Lys Leu Leu Pro Ser Val Val Leu Lys Leu Leu Leu Ala Ala Val
1               5                   10                  15

Leu Ser Ala Leu Val Thr Gly Glu Ser Leu Glu Gln Leu Arg Arg Gly
            20                  25                  30

Leu Ala Ala Gly Thr Ser Asn Pro Asp Pro Ser Thr Gly Ser Thr Asp
        35                  40                  45

Gln Leu Leu Arg Leu Gly Gly Gly Arg Asp Arg Lys Val Arg Asp Leu
    50                  55                  60

Gln Glu Ala Asp Leu Asp Leu Leu Arg Val Thr Leu Ser Ser Lys Pro
65                  70                  75                  80

Gln Ala Leu Ala Thr Pro Ser Lys Glu Glu His Gly Lys Arg Lys Lys
                85                  90                  95

Lys Gly Lys Gly Leu Gly Lys Lys Arg Asp Pro Cys Leu Arg Lys Tyr
            100                 105                 110

Lys Asp Phe Cys Ile His Gly Glu Cys Lys Tyr Val Lys Glu Leu Arg
        115                 120                 125

Ala Pro Ser Cys Ile Cys His Pro Gly Tyr His Gly Glu Arg Cys His
    130                 135                 140

Gly Leu Ser Leu Pro Val Glu Asn Arg Leu Tyr Thr Tyr Asp His Thr
145                 150                 155                 160

Thr Ile Leu Ala Val Val Ala Val Val Leu Ser Ser Val Cys Leu Leu
                165                 170                 175

Val Ile Val Gly Leu Leu Met Phe Arg Tyr His Arg Arg Gly Gly Tyr
            180                 185                 190

Asp Val Glu Asn Glu Glu Lys Val Lys Leu Gly Met Thr Asn Ser His
        195                 200                 205

<210> SEQ ID NO 13
<211> LENGTH: 178
<212> TYPE: PRT
<213> ORGANISM: Homo sapiens

<400> SEQUENCE: 13

Met Asp Arg Ala Ala Arg Cys Ser Gly Ala Ser Ser Leu Pro Leu Leu
1               5                   10                  15

Leu Ala Leu Ala Leu Gly Leu Val Ile Leu His Cys Val Val Ala Asp
            20                  25                  30

Gly Asn Ser Thr Arg Ser Pro Glu Thr Asn Gly Leu Leu Cys Gly Asp
        35                  40                  45

Pro Glu Glu Asn Cys Ala Ala Thr Thr Thr Gln Ser Lys Arg Lys Gly
    50                  55                  60

His Phe Ser Arg Cys Pro Lys Gln Tyr Lys His Tyr Cys Ile Lys Gly
```

```
                65                  70                  75                  80
Arg Cys Arg Phe Val Val Ala Glu Gln Thr Pro Ser Cys Val Cys Asp
                    85                  90                  95

Glu Gly Tyr Ile Gly Ala Arg Cys Glu Arg Val Asp Leu Phe Tyr Leu
                100                 105                 110

Arg Gly Asp Arg Gly Gln Ile Leu Val Ile Cys Leu Ile Ala Val Met
                115                 120                 125

Val Val Phe Ile Ile Leu Val Ile Gly Val Cys Thr Cys Cys His Pro
            130                 135                 140

Leu Arg Lys Arg Lys Arg Lys Lys Glu Glu Met Glu Thr
145                 150                 155                 160

Leu Gly Lys Asp Ile Thr Pro Ile Asn Glu Asp Ile Glu Glu Thr Asn
                165                 170                 175

Ile Ala

<210> SEQ ID NO 14
<211> LENGTH: 87
<212> TYPE: PRT
<213> ORGANISM: Artificial
<220> FEATURE:
<223> OTHER INFORMATION: Synthesized

<400> SEQUENCE: 14

Met Thr Ser Gly His His His His His His Ser Ala Gly Val Asn Gly
1               5                   10                  15

Phe Val Asn Gln His Leu Cys Gly Ser His Leu Val Glu Ala Leu Tyr
                20                  25                  30

Leu Val Cys Gly Asp Arg Gly Phe Tyr Phe Asn Lys Pro Thr Gly Tyr
            35                  40                  45

Gly Ser Ser Ser Arg Arg Ala Pro Gln Thr Gly Ile Val Asp Glu Cys
        50                  55                  60

Cys Phe Arg Ser Cys Asp Leu Arg Arg Leu Glu Met Tyr Cys Ala Pro
65                  70                  75                  80

Leu Lys Pro Ala Lys Ser Ala
                85

<210> SEQ ID NO 15
<211> LENGTH: 190
<212> TYPE: PRT
<213> ORGANISM: Artificial
<220> FEATURE:
<223> OTHER INFORMATION: Synthesized

<400> SEQUENCE: 15

Met Val Lys Gln Ile Glu Ser Lys Thr Ala Phe Gln Glu Ala Leu Asp
1               5                   10                  15

Ala Ala Gly Asp Lys Leu Val Val Val Asp Phe Ser Ala Thr Trp Cys
                20                  25                  30

Gly His Cys Lys Met Ile Lys Pro Phe Phe His Ser Leu Ser Glu Lys
            35                  40                  45

Tyr Ser Asn Val Ile Phe Leu Glu Val Asp Val Asp Asp Ser Gln Asp
        50                  55                  60

Val Ala Ser Glu Ser Glu Val Lys Ser Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val Gly Ser Lys Ser Gly His His
```

```
                100                 105                 110
His His His His Ser Ala Lys Gly Gly Pro Arg Thr Leu Cys Gly Ala
            115                 120                 125

Glu Leu Val Asp Ala Leu Gln Phe Val Cys Gly Asp Arg Gly Phe Tyr
        130                 135                 140

Phe Asn Lys Pro Thr Gly Tyr Gly Ser Ser Ser Arg Arg Ala Pro Gln
145                 150                 155                 160

Thr Gly Ile Val Asp Glu Cys Cys Phe Arg Ser Cys Asp Leu Arg Arg
                165                 170                 175

Leu Glu Met Tyr Cys Ala Pro Leu Lys Pro Ala Lys Ser Ala
            180                 185                 190

<210> SEQ ID NO 16
<211> LENGTH: 191
<212> TYPE: PRT
<213> ORGANISM: Artificial
<220> FEATURE:
<223> OTHER INFORMATION: Synthesized

<400> SEQUENCE: 16

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
            20                  25                  30

Gly His Cys Lys Met Ile Lys Pro Phe Phe His Ser Leu Ser Glu Lys
            35                  40                  45

Tyr Ser Asn Val Ile Phe Leu Glu Val Asp Val Asp Asp Ser Gln Asp
        50                  55                  60

Val Ala Ser Glu Ser Glu Val Lys Ser Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val Gly Ser Lys Ser Gly His His
            100                 105                 110

His His His His Ser Ala Lys Gly Phe Val Asn Gln His Leu Cys Gly
            115                 120                 125

Ser His Leu Val Glu Ala Leu Tyr Leu Val Cys Gly Asp Arg Gly Phe
        130                 135                 140

Tyr Phe Asn Lys Pro Thr Gly Tyr Gly Ser Ser Ser Arg Arg Ala Pro
145                 150                 155                 160

Gln Thr Gly Ile Val Asp Glu Cys Cys Phe Arg Ser Cys Asp Leu Arg
                165                 170                 175

Arg Leu Glu Met Tyr Cys Ala Pro Leu Lys Pro Ala Lys Ser Ala
            180                 185                 190

<210> SEQ ID NO 17
<211> LENGTH: 175
<212> TYPE: PRT
<213> ORGANISM: Artificial
<220> FEATURE:
<223> OTHER INFORMATION: Synthesized

<400> SEQUENCE: 17

Met Val Lys Gly Lys His His His His His Asn Gly Lys Gly Lys
1               5                   10                  15

Ser Lys Val Arg Ser Ser Ser Arg Thr Pro Ser Asp Lys Pro Val Ala
            20                  25                  30
```

```
His Val Val Ala Asn Pro Gln Ala Glu Gly Gln Leu Gln Trp Leu Asn
            35                  40                  45

Arg Arg Ala Asn Ala Leu Leu Ala Asn Gly Val Glu Leu Arg Asp Asn
     50                  55                  60

Gln Leu Val Val Pro Ser Glu Gly Leu Tyr Leu Ile Tyr Ser Gln Val
 65                  70                  75                  80

Leu Phe Lys Gly Gln Gly Cys Pro Ser Thr His Val Leu Leu Thr His
                 85                  90                  95

Thr Ile Ser Arg Ile Ala Val Ser Tyr Gln Thr Lys Val Asn Leu Leu
            100                 105                 110

Ser Ala Ile Lys Ser Pro Cys Gln Arg Glu Thr Pro Glu Gly Ala Glu
            115                 120                 125

Ala Lys Pro Trp Tyr Glu Pro Ile Tyr Leu Gly Gly Val Phe Gln Leu
            130                 135                 140

Glu Lys Gly Asp Arg Leu Ser Ala Glu Ile Asn Arg Pro Asp Tyr Leu
145                 150                 155                 160

Asp Phe Ala Glu Ser Gly Gln Val Tyr Phe Gly Ile Ile Ala Leu
                165                 170                 175

<210> SEQ ID NO 18
<211> LENGTH: 89
<212> TYPE: PRT
<213> ORGANISM: Artificial
<220> FEATURE:
<223> OTHER INFORMATION: Synthesized

<400> SEQUENCE: 18

Met Val Lys Gly Lys His His His His His Asn Gly Lys Gly Lys
 1               5                  10                  15

Ser Lys Phe Val Asn Gln His Leu Cys Gly Ser His Leu Val Glu Ala
             20                  25                  30

Leu Tyr Leu Val Cys Gly Asp Arg Gly Phe Tyr Phe Asn Lys Pro Thr
             35                  40                  45

Gly Tyr Gly Ser Ser Ser Arg Arg Ala Pro Gln Thr Gly Ile Val Asp
     50                  55                  60

Glu Cys Cys Phe Arg Ser Cys Asp Leu Arg Arg Leu Glu Met Tyr Cys
 65                  70                  75                  80

Ala Pro Leu Lys Pro Ala Lys Ser Ala
                 85
```

FUSION PROTEINS CONTAINING INSULIN-LIKE GROWTH FACTOR-1 AND EPIDERMAL GROWTH FACTOR AND VARIANTS THEREOF AND USES THEREOF

BACKGROUND

Currently 1.3 million people are diagnosed with cancer each year in the United States alone, and over 500,000 die. Treatment for most types of cancers includes chemotherapy. Chemotherapy drugs are administered systemically and attack all cells of the body, particularly dividing cells, not just cancer cells. Thus, side effects from chemotherapy drugs are often severe. These include anemia, nausea, hair loss, and immune suppression, including neutropenia, due to depletion of white blood cells. The side effects often limit the dose of chemotherapy agents that can be administered.

Cancer cells are obligately glycolytic. That is, they must consume glucose for their energy needs and they consume it anaerobically, which yields less energy than aerobic respiration. As a consequence, cancer cells must consume a large amount of glucose. Perhaps to assist with acquiring glucose, cancer cells from many types of cancer have been observed to have more insulin receptors than normal cells. (Ayre, S. G., et al., 2000, *Medical Hypotheses* 55:330; Abita, J. F., et al., 1984, *Leukemia Res.* 8:213.) Recently, a method of cancer treatment termed insulin potentiation therapy (IPT) that attempts to exploit the insulin receptors of cancer cells has been introduced in the United States. (Ayre, S. G., et al., 2000, *Medical Hypotheses* 55:330.) The method involves administering insulin to cancer patients, followed a short time later by administering chemotherapy drugs. Lower doses of chemotherapy drugs are used, which reduces the side effects. It is purported that the insulin somehow potentiates the effect of the chemotherapeutic agents on the cancer cells, allowing the use of lower doses.

In vitro data is reported to show that when methotrexate is administered with insulin to breast cancer cells in tissue culture, the same percent cell killing is achieved with $10^4$ lower methotrexate concentrations than when methotrexate is administered alone. (Alabaster, O., et al., 1981, *Eur J. Cancer Clin. Oncol.* 17:1223.) Methotrexate is a folic acid analogue that leads to the depletion of tetrahydrofolate. This interferes with thymidine and purine synthesis, and hence DNA synthesis.

Insulin does not greatly stimulate uptake of chemotherapeutic agents. One study has shown only a 2-fold stimulation of uptake of elipticine by MDA-MB-231 breast cancer cells when the cells were incubated with insulin. (Oster, J. B., et al., 1981, *Eur J. Cancer Clin. Oncol.* 17:1097.) Another study showed a 50% stimulation of uptake of methotrexate by breast cancer cells when the cells were incubated with insulin. (Shilsky, R. L., et al., 1981, *Biochem. Pharmacol.* 30:1537.) Thus, the mechanism for insulin potentiation of methotrexate cytotoxicity must be primarily due to factors other than enhanced uptake.

Another receptor often found in greater numbers in cancer cells than in normal cells of the same tissue type is the insulin-type growth factor-1 receptor (IGF-1 receptor or IGF-1R). IGF-1 is a peptide of 70 amino acid residues having 40% identity with proinsulin. (Daughaday, W. H., et al., 1989, *Endocrine Revs.* 10:68.) Insulin and IGF-1 have some cross-reactivity with each other's receptor. (Soos, M. A., et al., 1993, *Biochem. J.* 290:419.) IGF-1 is secreted by the liver into the circulatory system and stimulates growth of many cell types. IGF-1 is also produced by many cell types throughout the body, including many cancers, for autocrine and paracrine effects. IGF-1 production is stimulated by growth hormone. (Stewart, C. H., et al., 1996, *Physiol. Revs.* 76:1005; Yakar, S., et al., 2002, *Endocrine* 19:239.)

To target the IGF receptor in cancer treatment, we have made compounds for treating cancer that have an anti-cancer chemotherapeutic agent linked to an insulin-like growth factor-1 (IGF-1) receptor ligand (WO 2005/041865; U.S. Pat. No. 8,501,906; US Published patent application 20100197890, all incorporated by reference).

Another receptor often found overexpressed in cancer cells is the epidermal growth factor receptor (EGFR or ErbB-1).

SUMMARY

Improved ligands to the IGF-1R (type I IGF receptor) that are advantageous for conjugating to chemotherapeutic agents are needed. Ligands to ErbB-1 that are advantageous for conjugation to chemotherapeutic agents are also needed. Improved expression in microbial hosts of cytokines is also desired.

We have synthesized a variant of IGF-1 we have named 765IGF having the sequence SEQ ID NO:2. SEQ ID NO:3 is the sequence of wild-type human IGF-1. Residues 19-88 of SEQ ID NO:2 are identical to wild type IGF-1 except that the Arginine at position 21 of SEQ ID NO:2 is a substitution of glutamic acid at position 3 of wild-type IGF-1 (SEQ ID NO:3). Residues 19-88 of SEQ ID NO:2 correspond to R3-IGF, a variant form of IGF-1 that has reduced binding for the soluble IGF-1 binding proteins (as compared to wild-type IGF-1). The soluble IGF-1 binding proteins are soluble proteins in blood that bind circulating IGF-1 tightly. When bound to soluble IGF-1 binding proteins, IGF-1 is not available to bind to the membrane IGF receptor (type 1 IGF receptor, IGF-1R). In order to more effectively target the IGF ligand portion of our IGF-chemotherapeutic-agent conjugates to the IGF-1 receptor, we wanted the ligand portion to be a variant having reduced binding affinity for the soluble IGF-1 binding proteins.

Residues 1-18 of 765IGF (SEQ ID NO:2) are a leader sequence that provides a polyhistidine purification tag and several lysine residues. The lysine residues have amino groups that are available for conjugation to chemotherapeutic agents. So it is possible to couple more chemotherapeutic agent to 765IGF than to wild type IGF-1 or R3-IGF.

We have also conjugated (covalently attached) methotrexate (MTX) to amino groups of 765IGF to make a 765IGF-MTX conjugate, and have shown that this conjugate inhibits growth of tumor cells in vitro.

765IGF has been found to have several surprising advantages:
The yield of purified 765IGF from a recombinant microbial host per liter of fermented microbial host is higher than other variants of IGF-1.
It binds at excellent affinity to the IGF receptor and displaces more wild type IGF-1 than does another variant of IGF-1, long-R3-IGF, suggesting that 765IGF may bind to a secondary site on cancer cells that IGF-1 binds to.
765IGF conjugated to methotrexate yields a higher loading of methotrexate (more methotrexate groups covalently attached per IGF molecule) than two other IGF variants—IGF132 and long-R3-IGF.
765IGF is more stable to storage than IGF132. IGF132 breaks down to produce a significant amount of smaller molecular weight fragments of IGF132. These smaller fragments are seen on SDS-PAGE. 765IGF is more stable in storage and produces less of these smaller fragments.

The leader sequence of 765IGF is SEQ ID NO:1. We have now used this same leader sequence as an N-terminal leader on other cytokines and other proteins expressed in *E. coli*, and in all cases tested so far it has allowed purification of the protein in excellent yield in active form.

Thus, one embodiment of the invention provides a polypeptide comprising SEQ ID NO:2.

Another embodiment provides a polypeptide comprising SEQ ID NO:1.

The amino terminal methionine of SEQ ID NO:1 and SEQ ID NO:2 is sometimes cleaved off of the polypeptide in *E. coli*, so one embodiment provides a polypeptide comprising residues 2-18 of SEQ ID NO:1.

Another embodiment provides a polypeptide comprising (a) SEQ ID NO:1 or residues 2-18 of SEQ ID NO:1 and (b) SEQ ID NO:3, SEQ ID NO:4, residues 2-54 of SEQ ID NO:9, residues 40-89 of SEQ ID NO:10, residues 101-184 of SEQ ID NO:11, residues 63-148 of SEQ ID NO:12, or residues 32-111 of SEQ ID NO:13, or a variant 90% or more identical to SEQ ID NO:3, SEQ ID NO:4, residues 2-54 of SEQ ID NO:9, residues 40-89 of SEQ ID NO:10, residues 101-184 of SEQ ID NO:11, residues 63-148 of SEQ ID NO:12, or to residues 32-111 of SEQ ID NO:13.

Another embodiment provides a compound comprising an anti-cancer chemotherapeutic agent covalently attached to a polypeptide comprising (a) SEQ ID NO:1 or residues 2-18 of SEQ ID NO:1 and (b) SEQ ID NO:3, SEQ ID NO:4, residues 2-54 of SEQ ID NO:9, residues 40-89 of SEQ ID NO:10, residues 101-184 of SEQ ID NO:11, residues 63-148 of SEQ ID NO:12, or residues 32-111 of SEQ ID NO:13, or a variant 90% or more identical to SEQ ID NO:3, SEQ ID NO:4, residues 2-54 of SEQ ID NO:9, residues 40-89 of SEQ ID NO:10, residues 101-184 of SEQ ID NO:11, residues 63-148 of SEQ ID NO:12, or to residues 32-111 of SEQ ID NO:13. Preferably the anti-cancer chemotherapeutic agent is covalently attached to lysine side chains of SEQ ID NO:1 in the polypeptide.

Another embodiment provides a method of inhibiting the growth of cancer cells comprising contacting the cancer cells with the compound comprising an anticancer chemotherapeutic agent covalently attached to a polypeptide comprising (a) SEQ ID NO:1 or residues 2-18 of SEQ ID NO:1 and (b) SEQ ID NO:3, SEQ ID NO:4, residues 2-54 of SEQ ID NO:9, residues 40-89 of SEQ ID NO:10, residues 101-184 of SEQ ID NO:11, residues 63-148 of SEQ ID NO:12, or residues 32-111 of SEQ ID NO:13, or a variant 90% or more identical to SEQ ID NO:3, SEQ ID NO:4, residues 2-54 of SEQ ID NO:9, residues 40-89 of SEQ ID NO:10, residues 101-184 of SEQ ID NO:11, residues 63-148 of SEQ ID NO:12, or to residues 32-111 of SEQ ID NO:13.

Likewise, another embodiment provides a method of treating cancer in a mammal comprising administering to the mammal the same compound.

It is believed that stimulating cancer cells to divide with IGF-1 at approximately the same time that radiation is administered (i.e, within approximately 6 hours before or after administration of the radiation) sensitizes the cancer cells to be killed by the radiation. (See US 20060258589.) Thus, one embodiment provides a method of treating cancer in a mammal comprising: administering a polypeptide comprising SEQ ID NO:2 or residues 2-88 of SEQ ID NO:2 to the mammal and administering radiation to the mammal.

Likewise, it is believed that stimulating cancer cells to divide with IGF-1 at approximately the same time that chemotherapy is administered (i.e, within approximately 6 hours before or after administration of the chemotherapy) sensitizes the cancer cells to be killed by the chemotherapy. (See U.S. Pat. No. 8,501,906.) Thus, one embodiment provides a method of treating cancer in a mammal comprising: administering to the mammal an anti-cancer chemotherapeutic agent and a polypeptide comprising SEQ ID NO:2 or residues 2-88 of SEQ ID NO:2.

Another embodiment provides a fusion polypeptide comprising: (a) SEQ ID NO:3, SEQ ID NO:4, residues 2-54 of SEQ ID NO:9, residues 40-89 of SEQ ID NO:10, residues 101-184 of SEQ ID NO:11, residues 63-148 of SEQ ID NO:12, or residues 32-111 of SEQ ID NO:13, or a variant 90% or more identical to SEQ ID NO:3, SEQ ID NO:4; residues 2-54 of SEQ ID NO:9, residues 40-89 of SEQ ID NO:10, residues 101-184 of SEQ ID NO:11, residues 63-148 of SEQ ID NO:12, or to residues 32-111 of SEQ ID NO:13; and (b) a polypeptide segment or segments N-terminal to (a) or C-terminal to (a) or both N-terminal to (a) and C-terminal to (a); wherein polypeptide segment or segments (b) total 3-40 amino acid residues and comprise 3-20 amino acid residues that are lysine residues or 3-20 amino acid residues that are aspartic acid or glutamic acid residues.

Another embodiment provides a compound comprising an anti-cancer chemotherapeutic agent covalently attached to the fusion polypeptide comprising: (a) SEQ ID NO:3, SEQ ID NO:4, residues 2-54 of SEQ ID NO:9, residues 40-89 of SEQ ID NO:10, residues 101-184 of SEQ ID NO:11, residues 63-148 of SEQ ID NO:12, or residues 32-111 of SEQ ID NO:13, or a variant 90% or more identical to SEQ ID NO:3, SEQ ID NO:4; residues 2-54 of SEQ ID NO:9, residues 40-89 of SEQ ID NO:10, residues 101-184 of SEQ ID NO:11, residues 63-148 of SEQ ID NO:12, or to residues 32-111 of SEQ ID NO:13; and (b) a polypeptide segment or segments N-terminal to (a) or C-terminal to (a) or both N-terminal to (a) and C-terminal to (a); wherein polypeptide segment or segments (b) total 3-40 (or 3-30, or 3-20) amino acid residues and comprise 3-20 amino acid residues that are lysine residues or 3-20 amino acid residues that are aspartic acid or glutamic acid residues. Preferably, the chemotherapeutic agent is covalently attached to the lysine residues or aspartic acid or glutamic acid residues of segment or segments (b) of the fusion polypeptide.

Another embodiment provides a method of inhibiting the growth of cancer cells comprising contacting the cancer cells with the compound comprising an anti-cancer chemotherapeutic agent covalently attached to the fusion polypeptide comprising: (a) SEQ ID NO:3, SEQ ID NO:4, residues 2-54 of SEQ ID NO:9, residues 40-89 of SEQ ID NO:10, residues 101-184 of SEQ ID NO:11, residues 63-148 of SEQ ID NO:12, or residues 32-111 of SEQ ID NO:13, or a variant 90% or more identical to SEQ ID NO:3, SEQ ID NO:4; residues 2-54 of SEQ ID NO:9, residues 40-89 of SEQ ID NO:10, residues 101-184 of SEQ ID NO:11, residues 63-148 of SEQ ID NO:12, or to residues 32-111 of SEQ ID NO:13; and (b) a polypeptide segment or segments N-terminal to (a) or C-terminal to (a) or both N-terminal to (a) and C-terminal to (a); wherein polypeptide segment or segments (b) total 3-40 amino acid residues and comprise 3-20 amino acid residues that are lysine residues or 3-20 amino acid residues that are aspartic acid or glutamic acid residues. Preferably, the chemotherapeutic agent is covalently attached to the lysine residues or aspartic acid or glutamic acid residues of segment or segments (b) of the fusion polypeptide.

Likewise, another embodiment provides a method of treating cancer in a mammal comprising administering to the mammal the same compound.

It is shown herein that a conjugate of bendamustine to a fusion protein comprising the soluble form of epidermal growth factor in a fusion protein with the leader sequence of SEQ ID NO:1 is effective to treat and in some cases cure cancer in a mouse in vivo model with a xenograft of a cancer cell line high in ErbB-1 (EGF) receptors. The bendamustine conjugate inhibited cell line growth of the same cell line at more than 1000-fold lower concentration than free bendamustine. Thus, one embodiment provides a compound comprising bendamustine covalently attached to a cytokine that is a ligand to ErbB-1. The cytokine may be part of a fusion protein, but is not necessarily part of a fusion protein.

DETAILED DESCRIPTION

Definitions

Figure 1:
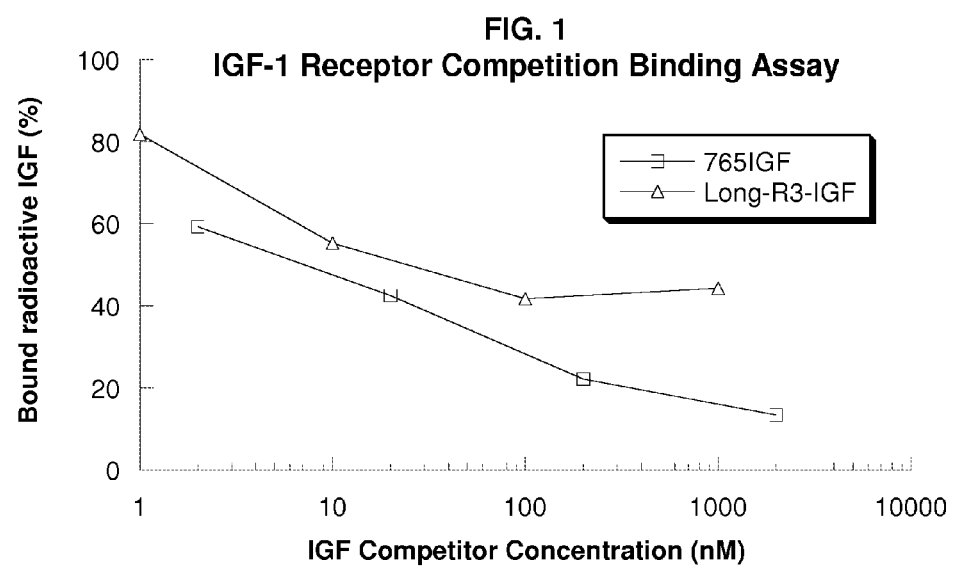
FIG. 1 shows the results of an IGF receptor binding assay showing % of radioactive signal bound (radioactive IGF-1) versus concentration of 765IGF or long-R3-IGF.

The term "anti-cancer chemotherapeutic agent" refers to a synthetic, biological, or semi-synthetic compound that is not an enzyme and that kills cancer cells or inhibits the growth of cancer cells while having less effect on non-cancerous cells.

The term "treating cancer" includes, e.g., preventing metastasis, inhibiting growth of a cancer, stopping the growth of cancer, or killing cells of a cancer.

The term "binding affinity" of a ligand for a particular receptor refers to the association constant $K_A$ (the inverse of the dissociation constant $K_D$) or to experimentally determined approximations thereof.

The term "anti-metabolite" refers to an anti-cancer chemotherapeutic agent that bears a structural similarity to a naturally occurring substance, interacts with enzymes as an inhibitor or a substrate, and interferes with cellular processes. Examples include methotrexate, fluorouracil, floxuridine, fludarabine, mercaptopurine, thioguanine, cytarabine, azacytidine, cladribine, and pentostatin.

The term "cytokine" refers to nonantibody proteins released by one cell population on contact with specific antigen, which act as intercellular mediators, as in the generation of an immune response. Cytokines include, for example, insulin, insulin-like growth factor 1 (IGF-1), epidermal growth factor, transforming growth factor alpha, transforming growth factor beta, and interleukins.

The "IGF-1 receptor" is also known in the literature as the type 1 IGF receptor.

"Containing" as used herein is open-ended; i.e, it allows the inclusion of other unnamed elements and has the same meaning as "comprising."

The "EGF receptor" as used herein, refers to ErbB-1.

Description

We have expressed in E. coli, from a recombinant vector with expression controlled by a T7 promoter and induced with IPTG, a fusion protein having the sequence of SEQ ID NO:2. This protein has the leader sequence at its N-terminus of SEQ ID NO:1, which provides a polyhis tag for purification and several additional lysine residues. The C-terminal of the protein is residues 19-88 and corresponds to R3-IGF, which is human wild type IGF-1 sequence with an arginine at position 21 of SEQ ID NO:2 that replaces the native glutamic acid at position 3 of wild-type IGF-1 (SEQ ID NO:3).

R3-IGF is a variant IGF-1, as discussed below.

765IGF (SEQ ID NO:2) comprising SEQ ID NO:1 as a leader sequence followed by R3-IGF expressed at a high yield and purified at a higher yield than other IGF fusion protein constructs comprising different leader sequences. It was more stable to storage than IGF132, another variant of IGF-1. It also refolded with almost 100% yield of active form, and it displaced more wild-type IGF-1 from its receptor on MCF7 cells than did long-R3-IGF, another variant of IGF-1.

The SEQ ID NO:1 leader also provides five lysine residues. A 765IGF-methotrexate conjugate was prepared by covalently attaching methotrexate through one of its carboxyl groups by amide bond to amino groups on 765IGF. 765IGF has nine amino groups, including eight lysine side chains (five of these in the SEQ ID NO:1 leader) and the amino terminal alpha-amino group. The 765IGF-MTX had an average of about 8 methotrexate groups attached per IGF monomer. Conjugates to longR3-IGF and IGF132 had fewer methotrexate groups per IGF monomer. So this was another advantage of the SEQ ID NO:1 leader.

A fusion protein called 765EGF with the SEQ ID NO:1 leader at the N-terminus fused to the sequence of mature soluble form EGF was also synthesized (SEQ ID NO:8). This also expressed from a recombinant vector under the control of a T7 promoter in E. coli to high yield and purified to good yield. It also refolded to a biologically active form.

The SEQ ID NO:1 leader is thus generally applicable for expressing proteins in good yield from microbial hosts, particularly E. coli, and for efficient purification in good yield. It is particularly applicable for expression of cytokines.

R3-IGF is a variant IGF-1 in a fusion protein with SEQ ID NO:1 in SEQ ID NO:2. It is a variant that activates the IGF receptor (IGF-1R) but has reduced binding affinity for the soluble IGF binding proteins (as compared to wild-type IGF-1) (Francis, G. L., et al. 1992, J. Mol. Endocrinol. 8:213-223; Tomas, F. M. et al., 1993, J. Endocrinol. 137: 413-421). Soluble IGF binding proteins are natural serum proteins that bind to IGF-1, holding it in circulation and extending its biological half-life. But when IGF-1 is bound to the IGF binding proteins it cannot bind to the membrane IGF receptor (IGF-1R). (Clemons, D. R., 1998, Mol. Cell.

Endocrinol. 140:19-24.) For that reason, variants of IGF-1 that have reduced binding to the soluble IGF binding proteins are more active in vivo than wild-type IGF-1 and more rapidly target the IGF receptor.

Binding affinity for IGF binding proteins can be tested with rat L6-myoblast-conditioned medium. The medium from growth of rat L6 myoblasts (0.2 ml) is mixed with 8,000 cpm $^{125}$I-IGF-1 (approximately 0.05 uCi) in 0.3 ml final volume of 50 mM sodium phosphate, pH 6.5, 0.25% bovine albumin and test competitor (wild type IGF-1 or an IGF variant) at 0.1 nM to 1 uM final concentration. After incubation 90 minutes at room temperature, to separate bound and free tracer an ice cold rapidly stirred suspension of charcoal at 5 mg/ml in assay buffer containing 0.2 mg/ml protamine sulfate is added to the sample, and after 8 minutes on ice, the mixture is centrifuged 20 minutes at 5,000×g. Radioactivity in the supernatant is counted in a gamma counter. The binding affinity of a variant can be compared to that of wild-type IGF to determine whether a variant has reduced binding affinity for the soluble IGF binding proteins.

Thus, in some embodiments, the polypeptides described herein comprise SEQ ID NO:1 and a variant IGF-1 that has reduced binding affinity for the soluble IGF binding proteins.

Some specific variants of IGF-1 with reduced binding affinity to the soluble IGF binding proteins include IGF132 (SEQ ID NO:4) (disclosed in U.S. Pat. No. 4,876,242), LONG-R3-IGF (SEQ ID NO:5), R3-IGF (SEQ ID NO:6), and des(1-3)IGF1 (SEQ ID NO:7), which lacks the first three residues of wild-type IGF-1. (LongR3-IGF, R3-IGF, and des(1-3)IGF1, are described in Francis, G. L., et al. 1992, *J. Mol. Endocrinol.* 8:213-223; Tomas, F. M. et al., 1993, *J. Endocrinol.* 137:413-421). Thus, in particular embodiments, the polypeptide that is a variant IGF-1 with reduced binding to the soluble IGF-1 binding proteins comprises any one of SEQ ID NOS:4-7.

The IGF receptor may be targeted in cancer with conjugates comprising (a) an anti-cancer chemotherapeutic agent covalently coupled to (b) an IGF receptor ligand such as IGF-1 or the IGF variants described herein in a polypeptide fusion comprising SEQ ID NO:1 or residues 2-18 of SEQ ID NO:1

Preferably, the IGF-1 receptor ligand with reduced affinity for soluble IGF-1 binding proteins has at least 5-fold, more preferably at least 10-fold, more preferably still at least 100-fold lower binding affinity for soluble IGF-1 binding proteins than wild-type IGF-1. Binding affinity for the soluble IGF-1 binding proteins can be measured by a competition binding assay against labeled IGF-1 (e.g., $^{125}$I IGF-1), using a mixture of purified IGF-1 binding proteins or rat L6 myoblast-conditioned medium (a naturally produced mixture of IGF-1 binding proteins), as described in Francis, G. L., et al. (1992, *J. Mol. Endocrinol.* 8:213-223); Szabo, L. et al. (1988, *Biochem. Biophys. Res. Commun.* 151:207-214); and Martin, J. L. et al. (1986, *J. Biol. Chem.* 261:8754-8760). Preferably, the variant IGF-1 has an IC$_{50}$ in a competition binding assay against labeled wild-type IGF-1 for binding to soluble IGF-1 binding proteins in L6 myoblast-conditioned medium of greater than 10 nM, more preferably greater than 100 nM.

Preferably, the variant IGF-1 with reduced affinity for soluble IGF-1 binding proteins has affinity for the IGF-1 receptor that is close to wild-type IGF-1 (e.g., less than 30-fold greater than wild-type IGF-1, more preferably less than 10-fold greater than wild-type IGF-1). In specific embodiments, the variant IGF-1 has an IC$_{50}$ in a competition binding assay against labeled wild-type IGF-1 for binding to IGF-1 receptors (e.g., on MCF-7 cells) of less than 50 nM, more preferably less than 10 nM, more preferably still less than 5 nM, more preferably still less than 3 nM). This assay is described in Ross, M. et al. (1989, *Biochem. J.* 258:267-272) and Francis, G. L., et al. (1992, *J. Mol. Endocrinol.* 8:213-223), and in Example 4 herein.

Another receptor often found in greater numbers in cancer cells than in normal cells of the same tissue type is the epidermal growth factor (EGF) receptor. (Nicholson, R. I. et al., 2001, *Eur. J. Cancer* 37:S9-S15. Kopp, R., et al., 2003, *Recent Results in Cancer Research* 162:115-132. Fox, S. B. et al., 1994, *Breast Cancer Res. Treat.* 29:41-49.) The EGF receptor, also known as ErbB-1, is activated by several agonists, including EGF itself, transforming growth factor alpha (TGFα), amphiregulin (AR), heparin-binding EGF-like growth factor (HB-EGF), and betacellulin (BTC). (Beerli, R. R. et al., 1996, *J. Biol. Chem.* 271:6071-6076. Earp, H. S., et al., 2003, *Trans. Am. Clin. Clim. Assoc.* 114:315-333.) Three other receptors are also considered members of the EGF family of receptors. They are ErbB-2, ErbB-3, and ErbB-4 (also known as HER2, HER3, and HER4, for human EGF receptor 2, 3, and 4, respectively). These receptors, especially ErbB-2, are also often overexpressed on cancerous cells. The receptors ErbB-2 and ErbB-4 are tyrosine kinases. The EGF receptor agonists listed above bind most strongly to the EGF receptor. They bind less tightly to the other receptors in the EGF receptor family. Neu differentiation factors (NDFs)/heregulins are ligands for EbrB-3 and ErbB-4. (Beerli, R. R., 1996, *J. Biol. Chem.* 271:6071-6076. Carraway, K. L. et al., 1994, *J. Biol. Chem.* 269:14303-14306. Plowman, G. D., et al., 1993, *Nature* 366:473-475.)

Thus, EGF, TGFα, amphiregulin, HB-EGF, BTC, and NDFs are also polypeptides that may be in fusion proteins with SEQ ID NO:1.

The sequence of a precursor of EGF is SEQ ID NO:9. In mature EGF, the amino terminal methionine of SEQ ID NO:9 is removed. (Gregory, H., 1975, *Nature* 257:325-327.) The sequence of the precursor of TGFα is SEQ ID NO:10. Mature TGFα is thought to be residues 40-89 of SEQ ID NO:10. (Qian, J. F., et al., 1993, *Gene* 132:291-296. Higashayaam, S., et al., 1991, *Science* 251:936-939.) The sequence of the precursor of amphiregulin is SEQ ID NO:11. Mature amphiregulin is thought to be residues 101-184 of SEQ ID NO:11. (Plowman, G. D., et al., 1990, *Mol. Cell. Biol.* 10:1969-1981.) The sequence of the precursor of HB-EGF is SEQ ID NO:12. Mature HB-EGF is thought to be residues 63-148 of SEQ ID NO:12. (Higashayama, S. et al., 1992, *J. Biol. Chem.* 267:6205-6212. Higashayaam, S., et al., 1991, *Science* 251:936-939.) The sequence of the precursor of betacellulin is SEQ ID NO:13. Mature betacellulin is thought to be residues 32-111 of SEQ ID NO:13. (Sasada, R. et al., 1993, *Biochem. Biophys. Res. Comm.* 190:1173-1179.) Cysteine residues 7 with 21, 15 with 32, and 34 with 43 of SEQ ID NO:9 form disulfide bridges to each other in mature EGF. (Gregory, H., 1975, *Nature* 257:325-327.) The homologous cysteine residues in the other natural EGF receptor ligands also form disulfide bridges. (Higashayaam, S., et al., 1991, *Science* 251:936-939.) Another polypeptide ligand to the EGF receptor is a chimera of sequences from natural EGF receptor ligands, e.g., the chimera E4T, which is a chimera of EGF and TGFα sequences, and is a more active agonist than either EGF or TGFα. (Lenferink, A. E. G., et al., 1998, *EMBO J.* 17:3385-3397. Kramer, R. H., et al., 1994, *J. Biol. Chem.* 269:8708-

8711.) Active chimeras that are agonists of ErbB-1 such as E4T may also be in fusion proteins with SEQ ID NO:1.

The fusion polypeptides comprising SEQ ID NO:1 or residues 2-18 of SEQ ID NO:1 and IGF-1 or a variant IGF-1 as described herein can also be used to enhance the effectiveness of chemotherapy or radiation by being administered to a cancer patient within 6 hours of administration of a chemotherapy agent or radiation therapy to the patient, as is described in WO 2005/041865 and U.S. Pat. No. 8,501,906 and U.S. Patent Application publication No. 20060258589.

Another embodiment of the invention provides a fusion protein comprising (a) IGF or an IGF variant or EGF or another ErbB-1 ligand or a variant thereof and (b) another polypeptide segment that provides additional amino acid residues to which a chemotherapeutic agent may be conjugated, particularly lysine, glutamic acid residues, or aspartic acid residues. IGF-1 has only 3 lysine residues and EGF has only 2 lysine residues. In order to have a higher loading of chemotherapeutic agent, we have found it is advantageous to have a fusion protein segment added to the IGF-1 or EGF segment (a) that has additional reactive amino acid residues, particularly lysine residues, to which a chemotherapeutic agent can be conjugated.

Thus, one embodiment of the invention provides a fusion polypeptide comprising: (a) SEQ ID NO:3, SEQ ID NO:4, residues 2-54 of SEQ ID NO:9, residues 40-89 of SEQ ID NO:10, residues 101-184 of SEQ ID NO:11, residues 63-148 of SEQ ID NO:12, or residues 32-111 of SEQ ID NO:13, or a variant 90% or more identical to SEQ ID NO:3, SEQ ID NO:4, residues 2-54 of SEQ ID NO:9, residues 40-89 of SEQ ID NO:10, residues 101-184 of SEQ ID NO:11, residues 63-148 of SEQ ID NO:12, or to residues 32-111 of SEQ ID NO:13; and (b) a polypeptide segment or segments N-terminal to (a) or C-terminal to (a) or both N-terminal to (a) and C-terminal to (a); wherein polypeptide segment or segments (b) total 3-40 (or 3-20 or 3-60 or 5-20 or 5-60) amino acid residues and comprise 3-20 amino acid residues that are lysine residues or 3-20 amino acid residues that are aspartic acid or glutamic acid residues.

In particular embodiments, the polypeptide segment or segments (b) comprises 3-20 (or 3-10 or 5-20 or 5-10) amino acid residues that are lysine. In a specific embodiment, at least 20% of the residues of segment or segments (b) are lysine residues.

In other embodiments, the polypeptide segment or segments (b) comprise 3-20 (or 3-10, or 5-10, or 5-10) amino acid residues that are aspartic acid or glutamic acid residues (i.e., the total of aspartic and glutamic acid residues equals the cited number). In a specific embodiment, at least 20% of the residues of segment or segments (b) are aspartic acid or glutamic acid residues.

In a specific embodiment of this fusion protein the polypeptide segment (a) comprises IGF-1 or a variant of IGF-1 at least 90% identical to any one of SEQ ID NOS:3 and 4.

In another specific embodiment of this fusion protein, the polypeptide segment (a) comprises residues 2-54 of SEQ ID NO:9, residues 40-89 of SEQ ID NO:10, residues 101-184 of SEQ ID NO:11, residues 63-148 of SEQ ID NO:12, or residues 32-111 of SEQ ID NO:13, or a variant 90% or more identical to residues 2-54 of SEQ ID NO:9, residues 40-89 of SEQ ID NO:10, residues 101-184 of SEQ ID NO:11, residues 63-148 of SEQ ID NO:12, or to residues 32-111 of SEQ ID NO:13.

Another embodiment of the invention provides a compound comprising a chemotherapeutic agent covalently attached to the fusion polypeptide comprising a ligand to ErbB-1 or IGFR1.

In a more specific embodiment, the chemotherapeutic agent is covalently attached to one or more lysine residue side chains of segment or segments (b) in the polypeptide.

In a more specific embodiment where the chemotherapeutic agent is covalently attached to one or more lysine residue side chains of segment or segments (b), the chemotherapeutic agent may be one with a free carboxyl group, such as methotrexate, chlorambucil, or bendamustine.

In specific embodiments of the methods described herein, the cancer treated is lung cancer, prostate cancer, colorectal cancer, breast cancer, pancreatic cancer, leukemia, liver cancer, stomach cancer, ovarian cancer, uterine cancer, testicular cancer, brain cancer, non-Hodgkin's lymphoma, Hodgkin's lymphoma, Ewing's sarcoma, osteosarcoma, neuroblastoma, rhabdomyosarcoma, melanoma, or brain cancer.

In specific embodiments of the methods with the conjugates comprising fusion proteins comprising a cytokine that is a ligand to ErbB-1, the cancer is an epithelial cell cancer.

In particular embodiments, the chemotherapeutic agent conjugated to the polypeptide is mechlorethamine, cyclophosphamide, ifosfamide, melphalan, chlorambucil, thiotepa, hexamethylmelamine, busulfan, carmustine, lomustine, semustine, streptozocin, decarbazine, vincristine, vinblastine, etoposide, teniposide, paclitaxel, docetaxel, daunorubicin, idarubicin, doxorubicin, epirubicin, dactinomycin, plicamycin, mitomycin C, bleomycin, mitoxantrone, methotrexate, fluorouracil, floxuridine, fludarabine, mercaptopurine, thioguanine, cytarabine, azacytidine, cladribine, pentostatin, cisplatin, carboplatin, mitotane, procarbazine, or amsacrine.

Guidelines for Coupling Anti-Cancer Chemotherapeutic Agents to Receptor Ligands

The natural ligands to the insulin and IGF-1 receptors are proteins, namely insulin, IGF-1, and IGF-2. Chemotherapeutic agents are typically coupled to proteins through the reactive groups present on proteins. These include the N-terminal alpha-amino group, the C-terminal alpha-carboxyl group, the side-chain amino group of lysine, the side-chain carboxyl groups of aspartic acid and glutamic acid, the side chain thiol of cysteine, and the side chain of arginine. Other reactive side chains found on proteins are the side-chain hydroxyl of serine and threonine, the hydroxyaryl of tyrosine, the imidazole of histidine, and the methionine side chain.

Many of the same reactive groups are found on chemotherapeutic agents and on non-proteinaceous ligands of the insulin and IGF-1 receptors. Thus, many of the principles of modification and cross-linking of proteins discussed herein also apply to modification and cross-linking of chemotherapeutic agents and non-proteinaceous ligands.

The chemistry and principles of protein conjugation and cross-linking are described in Wong, Shan S., *Chemistry of Protein Conjugation and Cross-Linking,* 1991, CRC Press, Boca Raton, Fla. Other sources for information on this chemistry include the Pierce Biochemistry catalog; and Greene, T. W., and Wutz, P. G. M., *Protecting Groups in Organic Synthesis,* second edition 1991, John Wiley & Sons, Inc., New York, and references cited therein.

The strongest nucleophile of amino acid side chains is the thiol of reduced cysteine side chains. The thiol reacts with most protein modifying reagents. Alpha-haloacetamides and maleimides are considered to react specifically with cysteine residues, particularly at pH 7.0 and below. Thiols also react by disulfide interchange with disulfide reagents.

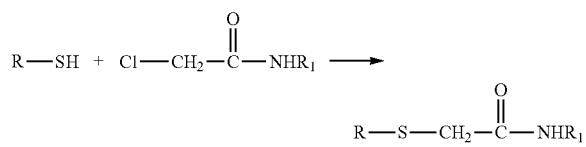

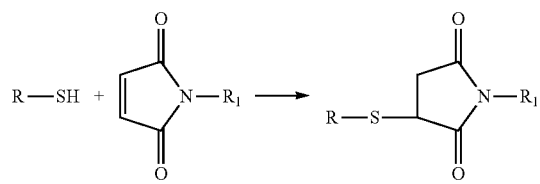

Amino groups are the next-strongest nucleophiles found on proteins. Aldehydes react with amino groups to form Schiff bases. The Schiff bases are hydrolyzable, which can be an advantage in the present invention. With uptake into cancer cells of a ligand-chemotherapeutic agent conjugate, in some cases it is necessary that the chemotherapeutic agent is cleaved from the conjugate for it to be active. This is better accomplished if the chemotherapeutic agent is linked to the ligand by a cleavable linkage, such as a hydrolyzable linkage. Cleavable linkages can be cleaved spontaneously or by enzymes in the cell. For instance, amide bonds are cleaved by certain enzymes, including proteases. A Schiff base linkage spontaneously hydrolyzes at an appreciable rate. A disulfide linkage is expected to be reductively cleaved in the intracellular reducing environment of a cancer cell.

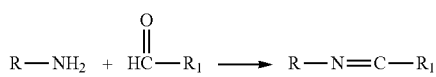

The Schiff base formed by reaction of an amino group with an aldehyde can be stabilized by reduction with, for instance, sodium borohydride or pyridine borane. Pyridine borane has the advantage of not reducing disulfides, which are found in insulin, IGF-1, and IGF-2 and are essential for the structure of those proteins.

Sugars or other moieties having hydroxyl groups on adjacent carbons, which are found in some chemotherapeutic agents, can be modified to react with amino groups by oxidizing the sugars with, for instance, periodate. This cleaves between the carbons and produces a dialdehyde. The aldehyde groups will react with amino groups.

A dialdehyde, such as glutaraldehyde, will cross-link two molecules having amino groups.

Other amino reagents include activated carbonyls, such as N-hydroxysuccinimide esters, p-nitrophenyl esters, or acid anhydrides (e.g., succinic anhydride).

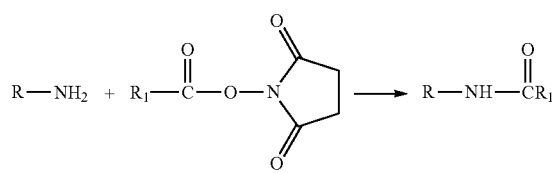

Amino groups also react with sulfonyl halides and aryl halides (e.g, 2,4-dinitrofluorobenzene).

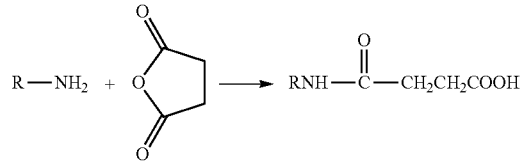

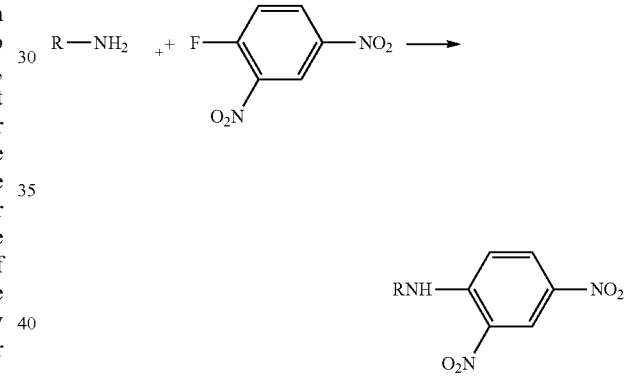

Amino groups also react with isocyanates and isothiocyanates to form urea or thiourea derivatives.

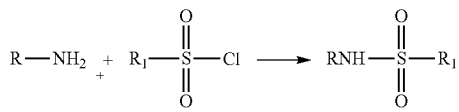

Imidoesters are the most specific acylating agents for amino groups. Imidoesters react specifically with amines to from imidoamides at pHs between about 7 and 10. This reaction has the advantage of maintaining charge stability by generating a positively charged group, the imidoamide, at the former amino group. Imidoamides also slowly hydrolyze at pHs above neutrality, which can also be an advantage in that the hydrolysis can release free chemotherapeutic agent in the cancer cell.

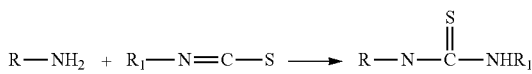

Carboxyl groups react specifically with diazoacetate and diazoacetamide under mild acid conditions, e.g., pH 5.

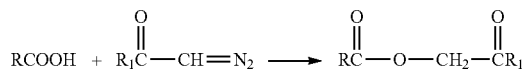

The most important chemical modification of carboxyls uses carbodiimides, such as 1-cyclohexyl-3-(2-morpholinyl-4-ethyl)carbodiimide (CMC) and 3-(3-dimethylaminopropyl)carbodiimide (EDC). In the presence of an amine, carbodiimides form an amide bond to the carboxyl in two steps. In the first step, the carboxyl group adds to the carbodiimide to form an O-acylisourea intermediate. Subsequent reaction with an amine yields the corresponding amide.

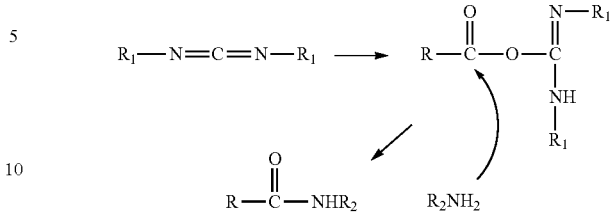

A particularly important carbodiimide reaction is its use in activating carboxyls with N-hydroxysuccinimide to form an N-hydroxysuccinimide ester.

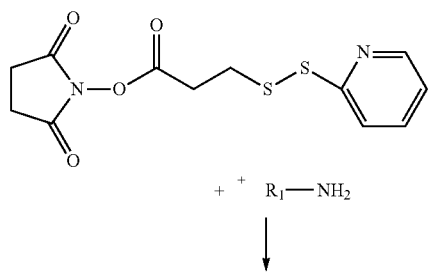

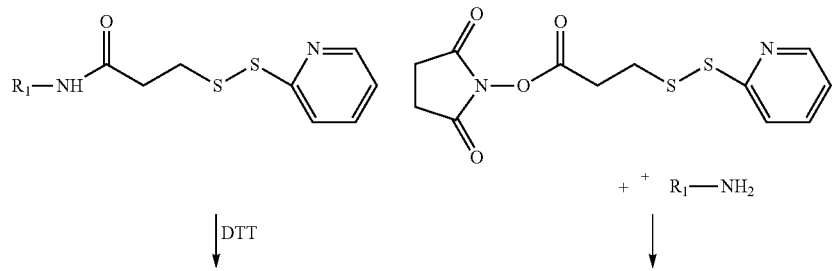

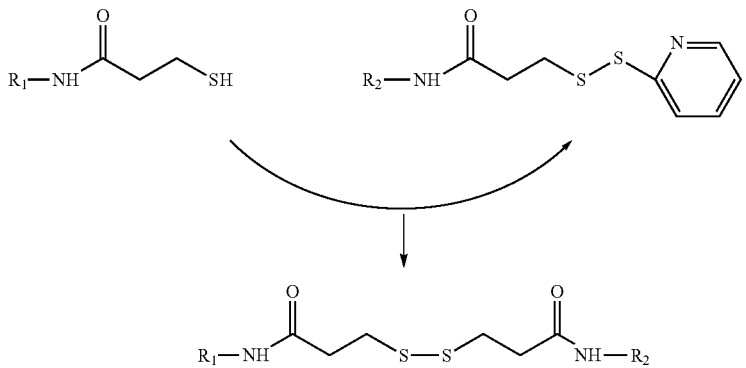

Arginine reacts with vicinal dialdehydes or diketones, such as glyoxal, 2,3-butanedione, and 1,2-cyclohexanedione. Borate may stabilize the adduct, if stabilization is desired.

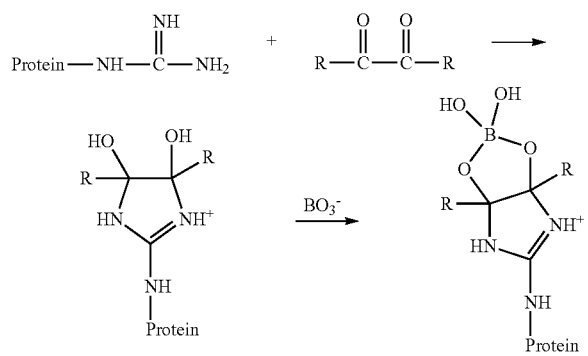

The reactive groups can also be interchanged with other reactive groups by some of the above reactions. For instance, modification of an amino group with an acid anhydride such as succinic anhydride, replaces the positively charged amino group with a free carboxyl group. Likewise, reaction of a carboxyl group with a carbodiimide and a diamine, such as ethylene diamine, replaces the carboxyl group with a free amino group.

Cross-Linking:

Reagents containing two of the reactive groups described above, for instance two amino-reactive groups or an amino-reactive and a thiol-reactive group, can be used to cross-link a chemotherapeutic agent containing one of the appropriate groups to an insulin or IGF-1 receptor ligand containing the other appropriate group. In addition, a carboxyl (of, e.g., a chemotherapeutic agent) activated with a carbodiimide or a carbodiimide and N-hydroxysuccinimide can react with an amino group (of, e.g., a protein ligand) to form an amide bond cross-link.

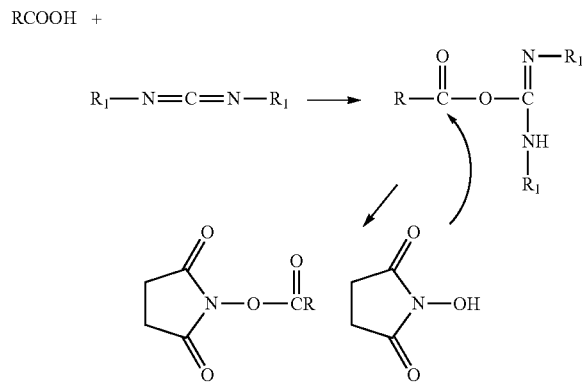

The activated carboxyl is stable enough to be isolated, but will then readily react with amino groups to form an amide bond.

Succinimides such as N-succinimidyl-3-[2-pyridyldithio] propionate (SPDP) can be used to couple two compounds through amino groups. (See Pierce Biotechnology catalog, and Thorpe, P. E. et al. 1982, *Immunol. Rev.* 62:119-158.)

Statements of Invention:

1. A polypeptide comprising SEQ ID NO:1 or comprising residues 2-18 of SEQ ID NO:1.
2. The polypeptide of statement 1 wherein the polypeptide has an N-terminus and SEQ ID NO:1 or residues 2-18 of SEQ ID NO:1 is at the N-terminus of the polypeptide.
3. The polypeptide of any of statements 1-2 wherein the polypeptide is a fusion protein further comprising a cytokine.
4. The polypeptide of statement 3 wherein the cytokine is a ligand to ErbB-1 or IGFR1.
4b. The polypeptide of statement 3 wherein the cytokine is tumor necrosis factor-alpha.
4c. The polypeptide of statement 4b wherein the polypeptide comprises SEQ ID NO:17 or residues 2-175 of SEQ ID NO:17.
5. The polypeptide of statement 4 wherein the polypeptide comprises (a) SEQ ID NO:1 or residues 2-18 of SEQ ID NO:1 and (b) SEQ ID NO:3, SEQ ID NO:4, residues 2-54 of SEQ ID NO:9, residues 40-89 of SEQ ID NO:10, residues 101-184 of SEQ ID NO:11, residues 63-148 of SEQ ID NO:12, or residues 32-111 of SEQ ID NO:13, or a variant 90% or more identical to SEQ ID NO:3, SEQ ID NO:4, residues 2-54 of SEQ ID NO:9, residues 40-89 of SEQ ID NO:10, residues 101-184 of SEQ ID NO:11, residues 63-148 of SEQ ID NO:12, or to residues 32-111 of SEQ ID NO:13.
5a. The polypeptide of statement 5 wherein segment (b) is SEQ ID NO:3, SEQ ID NO:4, or a variant 90% or more identical to SEQ ID NO:3 or to SEQ ID NO:4.
5b. The polypeptide of statement 5 wherein segment (b) is residues 2-54 of SEQ ID NO:9, residues 40-89 of SEQ ID NO:10, residues 101-184 of SEQ ID NO:11, residues 63-148 of SEQ ID NO:12, or residues 32-111 of SEQ ID NO:13, or a variant 90% or more identical to residues 2-54 of SEQ ID NO:9, residues 40-89 of SEQ ID NO:10, residues 101-184 of SEQ ID NO:11, residues 63-148 of SEQ ID NO:12, or to residues 32-111 of SEQ ID NO:13.
5c. The polypeptide of statement 5b wherein segment (b) is residues 2-54 of SEQ ID NO:9.
5d. The polypeptide of statement 5 wherein segment (b) is a variant of 90% or more identical to SEQ ID NO:3 selected from SEQ ID NO:6 and SEQ ID NO:7.
6. The polypeptide of statement 5 wherein the polypeptide comprises SEQ ID NO:2 or residues 2-88 of SEQ ID NO:2.
7. A compound comprising an anti-cancer chemotherapeutic agent covalently attached to the polypeptide of statement 5.
8. The compound of statement 7 wherein the chemotherapeutic agent is covalently attached to one or more lysine residue side chains of residues 2-18 of SEQ ID NO:1 in the polypeptide.
9. The compound of statement 7 wherein the chemotherapeutic agent is methotrexate.
10. The compound of statement 5 wherein the chemotherapeutic agent is selected from the group consisting of methotrexate, chlorambucil, and bendamustine.
11. The compound of statement 9 comprising methotrexate covalently attached to a polypeptide comprising SEQ ID NO:2 or residues 2-88 of SEQ ID NO:2.
12. The compound of statement 11 wherein the methotrexate is attached by amide bonds between carboxyl groups of the chemotherapeutic agent and amino groups of the polypeptide.
13. A method of inhibiting the growth of cancer cells comprising contacting the cancer cells with a compound of any one of statements 7-12.
14. The method of statement 13 wherein the contacting is in vitro.

15. The method of statement 13 wherein the contacting is in vivo.

16. The method of statement 15 wherein the contacting is in vivo in a human.

17. The method of statement 15 wherein the contacting is in vivo in a nonhuman mammal.

18. A method of treating cancer in a mammal comprising: administering to the mammal a compound of any one of statements 7-12.

19. The method of statement 18 wherein the mammal is not a human.

20. The method of statement 18 wherein the mammal is a human.

21. A method of treating cancer in a mammal comprising: administering a polypeptide comprising SEQ ID NO:2 or residues 2-88 of SEQ ID NO:2 to the mammal and administering radiation to the mammal.

22. A method of treating cancer in a mammal, comprising: administering to the mammal an anti-cancer chemotherapeutic agent and a polypeptide comprising SEQ ID NO:2 or residues 2-88 of SEQ ID NO:2.

23. A fusion polypeptide comprising:
(a) SEQ ID NO:3, SEQ ID NO:4, residues 2-54 of SEQ ID NO:9, residues 40-89 of SEQ ID NO:10, residues 101-184 of SEQ ID NO:11, residues 63-148 of SEQ ID NO:12, or residues 32-111 of SEQ ID NO:13, or a variant 90% or more identical to SEQ ID NO:3, SEQ ID NO:4; residues 2-54 of SEQ ID NO:9, residues 40-89 of SEQ ID NO:10, residues 101-184 of SEQ ID NO:11, residues 63-148 of SEQ ID NO:12, or to residues 32-111 of SEQ ID NO:13; and
(b) a polypeptide segment or segments N-terminal to (a) or C-terminal to (a) or both N-terminal to (a) and C-terminal to (a);
wherein polypeptide segment or segments (b) total 3-40 amino acid residues and comprise 3-20 amino acid residues that are lysine residues or 3-20 amino acid residues that are aspartic acid or glutamic acid residues.

23a. The fusion polypeptide of statement 23 wherein segment (b) is SEQ ID NO:1 or residues 2-18 of SEQ ID NO:1 and is N-terminal to segment (a).

23b. The fusion polypeptide of statement 23 wherein polypeptide segment or segments (b) comprise 3-10 amino acid residues that are lysine residues or 3-10 amino acid residues that are aspartic acid or glutamic acid residues.

24. The fusion polypeptide of statement 23 wherein the polypeptide segment (b) comprises 3-20 amino acid residues that are lysine.

25. The fusion protein of statement 23 or 24 wherein the polypeptide segment (a) comprises IGF-1 or a variant of IGF-1 at least 90% identical to any one of SEQ ID NOS:3 and 4.

26. The fusion protein of statement 23 or 24 wherein the polypeptide segment (a) comprises residues 2-54 of SEQ ID NO:9, residues 40-89 of SEQ ID NO:10, residues 101-184 of SEQ ID NO:11, residues 63-148 of SEQ ID NO:12, residues 32-111 or SEQ ID NO:13, or a variant 90% or more identical to residues 2-54 of SEQ ID NO:9, residues 40-89 of SEQ ID NO:10, residues 101-184 of SEQ ID NO:11, residues 63-148 of SEQ ID NO:12, or to residues 32-111 of SEQ ID NO:13.

27. A compound comprising a chemotherapeutic agent covalently attached to the fusion polypeptide of any one of statements 23-26.

27a. The compound of statement 27 wherein the polypeptide segment (a) comprises SEQ ID NO:3 or SEQ ID NO:4 or a variant at least 90% identical to any one of SEQ ID NOS:3 and 4.

27b. The compound of statement 27a wherein the fusion polypeptide comprises SEQ ID NO:2 or residues 2-88 of SEQ ID NO:2.

27c. The compound of statement 27 wherein the polypeptide segment (a) comprises residues 2-54 of SEQ ID NO:9, residues 40-89 of SEQ ID NO:10, residues 101-184 of SEQ ID NO:11, residues 63-148 of SEQ ID NO:12, residues 32-111 or SEQ ID NO:13, or a variant 90% or more identical to residues 2-54 of SEQ ID NO:9, residues 40-89 of SEQ ID NO:10, residues 101-184 of SEQ ID NO:11, residues 63-148 of SEQ ID NO:12, or to residues 32-111 of SEQ ID NO:13.

28. The compound of statement 27 wherein the chemotherapeutic agent is covalently attached to one or more lysine residue side chains of segment (b) in the polypeptide.

29. The compound of statement 28 wherein the chemotherapeutic agent is methotrexate.

30. The compound of statement 28 wherein the chemotherapeutic agent is selected from the group consisting of methotrexate, chlorambucil, and bendamustine.

31. The compound of statement 27 wherein the chemotherapeutic agent is covalently attached to one or more aspartic acid or glutamic acid side chains of segment (b) in the polypeptide.

32. A method of inhibiting the growth of cancer cells comprising contacting the cancer cells with a compound of any one of statements 27-31.

33. The method of statement 32 wherein the contacting is in vitro.

34. The method of statement 32 wherein the contacting is in vivo.

35. The method of statement 34 wherein the contacting is in vivo in a human.

36. The method of statement 34 wherein the contacting is in vivo in a nonhuman mammal.

37. A method of treating cancer in a mammal comprising: administering to the mammal a compound of any one of statements 27-31.

38. The method of statement 37 wherein the mammal is not a human.

39. The method of statement 37 wherein the mammal is a human.

40. A method of treating cancer in a mammal comprising: administering to the mammal a compound comprising a polypeptide comprising a cytokine that is a ligand to ErbB-1 covalently attached to bendamustine.

41. The method of statement 40 wherein the polypeptide is a fusion protein comprising one or more non-cytokine segments N-terminal or C-terminal to the cytokine.

42. The method of statement 40 wherein the cytokine is residues 2-54 of SEQ ID NO:9, residues 40-89 of SEQ ID NO:10, residues 101-184 of SEQ ID NO:11, residues 63-148 of SEQ ID NO:12, residues 32-111 or SEQ ID NO:13, or a variant 90% or more identical to residues 2-54 of SEQ ID NO:9, residues 40-89 of SEQ ID NO:10, residues 101-184 of SEQ ID NO:11, residues 63-148 of SEQ ID NO:12, residues 32-111 or SEQ ID NO:13.

43. The method of statement 40 wherein the polypeptide comprises SEQ ID NO:8.

44. A compound comprising bendamustine covalently attached to a polypeptide comprising a cytokine that is a ligand to ErbB-1.

EXAMPLES

Plasmids were synthesized by DNA 2.0 (Menlo Park, Calif.) encoding these proteins with nucleotide sequences optimized for expression in *E. coli*, and under the control of a T7 promoter:

| Protein encoded | Description | Sequence |
|---|---|---|
| 403IGF | His6-IGF | SEQ ID NO: 14 |
| 764IGF | His6-K5-IGF132 | SEQ ID NO: 18 |
| 765IGF | His6-K5-R3IGF | SEQ ID NO: 2 |
| 784IGF | mutTrx-R3IGF | SEQ ID NO: 15 |
| 785IGF | mutTrx-IGF132 | SEQ ID NO: 16 |

E. coli BL21(DE3) was transformed with each of the plasmids and transformants isolated. 10 ml of the transformed BL21(DE3) culture of each was used to seed 500 ml of LB media with 50 ug/ml kanamycin (LB-kan) in a 2 L baffled flask. These were induced with 0.4 mM final IPTG at an O.D. 600 nm of 0.6 and grown overnight at 25 degrees C.

The cells were resuspended in 50 mM Tris-HCl pH 8.0 and frozen. They were thawed and incubated at 5% wet weight/volume cell weight in 50 mM Tris-HCl pH 8.0, 0.2% Triton-X100, 0.5 mg lysozyme per g cell paste, for 30 minutes at room temperature. They were then sonicated to break cells. MgCl$_2$ was added to 3 mM final concentration and 250 ul of BENZONASE was added per liter of culture. This was incubated a further 1 hour at room temperature.

Inclusion bodies were isolated by centrifugation. Soluble fraction was retained.

Inclusion bodies were solubilized in 7 M urea, 0.5 M NaCl, 20 mM phosphate pH 7.8.

The solubilized inclusion bodies were loaded onto 1 ml of Ni-nitrolito-triacetic acid (Ni-NTA) resin in a column. The column was washed with Ni-A buffer and eluted with Ni-B buffer.
Ni-A 6 M urea, 0.5 M NaCl, 20 mM sodium phosphate, 20 mM imidazole, pH 7.3.
Ni-B 6 M urea, 0.5 M NaCl, 20 mM sodium phosphate, 0.4 M imidazole, pH 7.3.
The protein yields were:
403IGF eluate 3.6 mg
764IGF eluate 16 mg
765IGF eluate 24 mg
784IGF eluate 6.7 mg
785IGF eluate 1.9 mg
SDS-PAGE was run of the eluates and of the crude insoluble and soluble fractions. It appeared that 784IGF and 785IGF had about half of the IGF in the soluble fraction and half in the insoluble. 403IGF, 764IGF, and 765IGF appeared to have nearly all of the IGF in the insoluble fraction.

From this data, the best yield was with 765IGF. Those with the SEQ ID NO:1 leader sequence (764IGF and 765IGF) gave better yields than those with a simple Met-His6 leader (403IGF) or with thioredoxin leader sequences (784IGF and 785IGF). And the constructs with the R3IGF mutant for the IGF portion (765IGF and 784IGF) gave better yields than the corresponding constructs with the IGF132 mutant for the IGF portion of the fusion protein (764IGF and 785IGF).

Example 2

Refolding and Binding Assay 2 ml of each of the original Ni eluates from Example 1 was mixed with about an equal volume of 100 mM glycine, 6 M urea, pH 9.5, concentrated by ultrafiltration in a CENTRICON 3 kDa filter unit, then brought up again in that buffer and concentrated to about 420 ul. Then they were diluted to 2 mg/ml for 403IGF, 764IGF, and 765IGF, and 4 mg/ml for 784IGF and 2.4 mg/ml for 785IGF.

200 ul of each of these was mixed rapidly with 1.8 ml of refold buffer. Refold buffer was 1.4 M urea, 100 mM glycine, 0.5 M NaCl, 19% ethanol, 0.5 mM GSSG, 4 mM GSH, pH 9.5. They were refolded at room temperature for 3 hours, and then tested in a binding assay for competition binding to IGF receptors against 1-132 radioactive wild type IGF (Perkin Elmer, Inc.) For comparison, commercial Long-R3-IGF (LR3IGF) was also tested.

The approximate binding constants (KDs) in this experiment were these:

| LR3IGF | 1 nM |
|---|---|
| 403IGF | 2 nM |
| 764IGF | 100 nM |
| 765IGF | 10 nM |
| 784IGF | 3 nM |
| 785IGF | 40 nM |

The fusion proteins containing the R3IGF mutant (LR3IGF, 765IGF, and 784IGF) had lower $K_D$s than those containing the IGF132 mutant (403IGF, 764IGF and 785IGF).

Example 3

Purification and Yield of 765IGF

A plasmid encoding 765IGF with optimized codon usage for E. coli, with the 765IGF gene under the control of a T7 promoter, was synthesized by DNA 2.0 (Menlo Park, Calif., USA). E. coli B121(DE3) was transformed with the plasmid and grown in fermentor culture and induced with IPTG.

765IGF was purified under denaturing conditions by ion exchange chromatography and Nickel affinity chromatography. The yield of purified 765IGF was about 60 mg per liter of culture.

765IGF was refolded by a procedure similar to that of Example 2 and then the refolded protein was purified by ion exchange chromatography.

Example 4

765IGF Binding Assay to IGF-1 Receptor

Method:
Theory of Assay:
Radioactive $^{125}$I labeled insulin-like growth factor-1 (IGF-1) competes with a test ligand for binding to type 1 IGF receptors that are abundant on MCF7 cells (a human breast cancer cell line) in vitro. The tested ligands include our 765IGF variant of insulin-like growth factor-1 (IGF-1) and our novel covalent conjugates that contain the antifolate drug methotrexate coupled to 765IGF, as well as commercially available long-R3-IGF-1 (Sigma Aldrich, St. Louis, Mo., USA) as a comparison and positive control.

MCF7 cell media: 500 mL MEM, 0.01 mg/mL bovine insulin; 5 mL sodium pyruvate, 5 mL non-essential amino acids, 10 mL sodium bicarbonate, 10 mL fetal bovine serum, 5 mL penicillin/streptomycin.

MCF7 cells (ATCC HTB-22) were plated at 20,000 cells per well in a volume of 0.5 mL/well in a 48-well tissue culture plate (flat bottom with low evaporation lid) and placed in a cell culture incubator set at 37° C. with 5% CO$_2$. After 2-3 days in culture the plates were washed 2× with 0.5 mL per well of cold binding assay buffer (100 mM Hepes-NaOH, pH 7.2; 120 mM NaCl; 5 mM KCl, 1.2 mM MgSO4;

0.1% BSA). After the final wash, 0.5 mL of binding assay buffer was added to each well and the plates are placed at 4° C. for 2 to 6 hours.

Test ligands were prepared at a concentration of 10 micromolar (long-R3-IGF) or 20 micromolar (765IGF and IGF-MTX) in 5 mM HCl in a volume of 200 ul. To determine the concentration, the molecular weight of 765IGF (9742 daltons) and long-R3-IGF (9111 daltons) are used. For long-R3, the lyophilized commercial material is dissolved at 1.0 mg/ml in 10 mM HCl and this is diluted to a concentration of 91 ug/ml for a 10 uM solution.

The 765IGF and long-R3-IGF were diluted into binding buffer in the wells at concentrations of 2000 nM to 1 nM.

Next, 25 uCi lot of I-125 IGF (Perkin Elmer Radiochemicals, Waltham, Mass., USA) was dissolved in 1 ml of water. An appropriate dilution into binding buffer ws made, and then 50 ul of diluted radioactive IGF is added to each well, to add 0.03 uCi or more per well. For fresh I-125 IGF, per plate used 100 ul of the 1 ml solution of I-125 IGF in water can be added to 2.6 ml of binding buffer per plate used, and 50 ul added per well.

The plates were then incubated overnight at 4° C. Then the liquid was withdrawn from each well with a micropipettor and the wells were washed twice in binding buffer. Cells were lysed with 0.5 mL 300 mM NaOH, 1% SDS and the lysates were counted on a gamma counter.

Results:

The result of an IGF-1 receptor binding assay for 765IGF and commercially available long-R3-IGF are shown in FIG. 1. At high concentrations, 765IGF consistently displaced more radioactivity than long-R3-IGF, suggesting it may bind to IGF-1 binding sites on the membranes that long-R3-IGF does not. The $K_D$ of 765IGF in this assay was less than 1 nM, while the $K_D$ of long-R3-IGF was about 3 nM.

Example 5

Conjugation of Methotrexate to 765IGF

The protein was buffer exchanged into pH 7.3 conjugation buffer and adjusted to a concentration of 2.5 mg/ml.

pH 7.3 conjugation buffer: 25 mM sodium phosphate, 10 mM NaCl, 6 M urea, pH 7.3.

pH 6.3 conjugation buffer is the same buffer at pH 6.3. Methotrexate was dissolved at 20 mg/ml in pH 6.3 conjugation buffer, and the pH adjusted to pH 6.3 with NaOH.

1-ethyl-3-[3-dimethylaminopropyl]carbodiimide hydrochloride (EDC) was freshly dissolved in pH 6.3 conjugation buffer at 75 mg/ml.

One volume of EDC solution was added to 1 volume of MTX solution and incubated 30 seconds at room temperature and then this mixture was added to 8 volumes of 2.5 mg/ml protein solution in pH 7.3 conjugation buffer.

The mixture was mixed and then reacted overnight at room temperature. Then 6 M HCl was added to the reaction mixture to 60 mM final concentration. Then the reaction mixture was buffer exchanged into 10 mM HCl.

Result:

The amount of methotrexate conjugated per mole of protein was determined by measuring absorbance of the conjugate at 305 nm in 100 mM HCl, using a molar extinction coefficient for methotrexate groups of 21.6 per mM (Chamberlin et al. Analytical Profiles of Drug Substances, 1976, 5:283-306.) The protein concentration was determined by quantitative amino acid analysis. By this, the molar ratio of MTX groups to IGF in the 765IGF-MTX conjugate was approximately 8.

Example 6

765IGF-MTX In Vitro Cytotoxicity Assay

Cytotoxicity Assay.

This potency assay is an assay for inhibition of proliferation of MCF-7 tumor cells in vitro by incubation with the 765IGF-MTX.

Method

Day 0.

Five-thousand MCF7 cells were plated per well in a 96-well test plate in 100 ul of rich media on day 0.

Day 1.

A shadow plate was made for each test plate, with each well of the shadow plate containing media or 3× the intended final concentration of test agent in media in each well. As a negative control, media is used. As a positive control, free methotrexate at 3 uM is used.

After making the shadow plate, 50 ul is transferred from each well of the shadow plate to the corresponding well of the test plate to generate the final concentrations of test agent in the wells of the test plate.

Day 5.

Cell proliferation is determined by adding Dojindo CCK-8 reagent and incubating and measuring absorbance of the dye according to the manufacturer's instructions.

Figure 2:
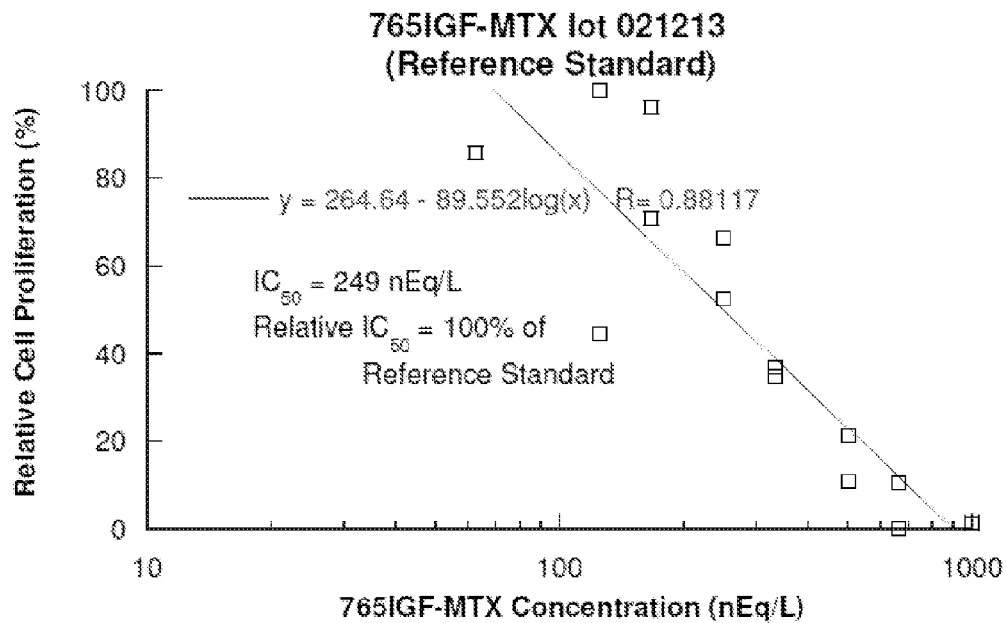
FIG. 2 shows a plot of MCF7 cell growth inhibition by 765IGF-MTX used to determine an $IC_{50}$ of 765IGF-MTX for growth inhibition.

Result:

Results of a representative cytotoxicity assay with 765IGF-MTX are shown in FIG. 2. The $IC_{50}$ (Concentration needed for 50% inhibition of cell proliferation) of 765IGF-MTX was 249 nEquivalents per L. (A nanoEquivalent is a nanomole of methotrexate groups conjugated to 765IGF.) For comparison, in the same assay, the $IC_{50}$ of free methotrexate was measured as 88 nM.

For comparison, an LR3IGF-MTX conjugate (methotrexate conjugated to long-R3-IGF) had an $IC_{50}$ of about 400 nEq/L (McTavish et al., 2009, Translational Research 153: 275-282).

Example 7

Inhibition of Dihydrofolate Reductase by Methotrexate and IGF-Methotrexate Conjugates Method:

The experiments were done with the dihydrofolate reductase assay kit from Sigma-Aldrich (St. Louis, Mo., USA), according to the manufacturer's instructions. In the assay dihydrofolate reductase is mixed with pH 7.5 buffer. Next the inhibitor—methotrexate or an IGF-methotrexate conjugate—is added and the solution mixed. It was incubated for 30 seconds to allow inhibitor binding. Then NADPH is added to 50 uM final concentration, and then dihydrofolic acid is added to 60 uM final concentration. The reaction is monitored by measuring absorbance at 340 nm.

Results:

The tested conjugates were:

765IGF-MTX prepared as described in Example 4. 765IGF has 9 amino groups available to conjugate to methotrexate (8 lysines and the N-terminal amino group). This batch had a MTX:protein molar ratio of 7.5.

765IGF-MTX 1/3. This conjugate was prepared with 1/3 of the usual concentrations of MTX and EDC in the conjugation reaction. It produced a conjugate with a MTX:protein molar ratio of 1.2.

LR3IGF-MTX. In this case, the version of IGF is long-R3-IGF. This has 4 available amino groups for conjugation (3 lysine side chains and the N-terminal amino group). This conjugate had a MTX:protein ratio of 2.8.

In addition, free methotrexate was tested.

Figure 3:
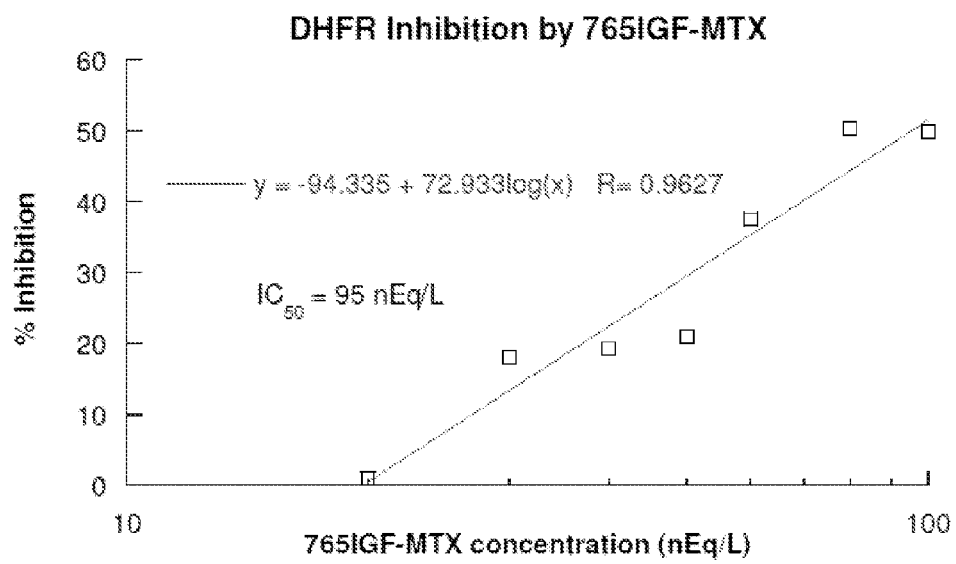
FIG. 3 shows the results of an assay for inhibition of dihydrofolate reductase (DHFR) by 765IGF-MTX.

The conjugates were exhaustively ultrafiltered to remove any free methotrexate before their use in the inhibition assay. A plot of the inhibition data for 765IGF-MTX is shown in FIG. 3.

The $IC_{50}$s of methotrexate and the conjugates were these:

| Competitor | $IC_{50}$ | MTX:IGF ratio |
|---|---|---|
| Methotrexate | 5.3 nM | N.A. |
| 765IGF-MTX | 95 nEq/L | 7.5 |
| 1/3 765IGF-MTX | 90 | 1.2 |
| LR3IGF-MTX | 99 | 2.8 |

The $IC_{50}$ in nEq/L was approximately the same for all three of the IGF-MTX conjugates, despite having different numbers of MTX groups conjugated per IGF protein monomer. This shows that each conjugated methotrexate group acts as an independent inhibitor of the enzyme. If the additional methotrexate groups on a conjugate monomer were sterically unable to bind to and inhibit a DHFR enzyme once one group is bound to a DHFR enzyme, then one would expect that the $IC_{50}$ for the conjugates would be the same in terms of nM protein concentration for each of the conjugates, instead of being the same in terms of nEq/L MTX group concentration, as is observed. Because the inhibition is proportional to MTX groups, 765IGF-MTX, with its higher MTX loading, has an inhibition constant in terms of protein concentration of 13 nM (95 nEq/L divided by 7.5 MTX per IGF gives 13 nM IGF), whereas LR3IGF-MTX has an inhibition constant in terms of protein concentration of 35 nM. Thus, with the higher loading of MTX, less 765IGF protein needs to be used to achieve the same inhibition of DHFR, and by inference the same level of killing of tumor cells.

The data show that the protein-conjugated MTX groups inhibit DHFR, but a higher concentration is needed for inhibition as compared to free MTX.

Example 8

765EGF

The protein 765EGF, having SEQ ID NO:8 was synthesized:

(SEQ ID NO: 8)
MVKGKHHHHHHNGKGKSK NSDSECPLSH DGYCLHDGVC MYIEALDKYA

CNCVVGYIGE RCQYRDLKWW ELR.

The underlined portion above is the SEQ ID NO:1 leader sequence, also found in 765IGF. The non-underlined portion is the amino acid sequence of mature soluble form of human epidermal growth factor. A plasmid encoding this protein, with optimized codon usage for E. coli, under the expression control of the T7 promoter, was synthesized by DNA 2.0 (Menlo Park, Calif., USA). E. coli BL21(DE3) was transformed with the plasmid and used to express the protein. The protein was expressed with growth in 2XYT medium+2.1 g/L dextrose, 50 ug/ml kanamycin. It was induced with 0.4 mM IPTG, and harvested 5 hours later.

The 765EGF protein was found in inclusion bodies. The inclusion bodies were isolated and solubilized and the 765EGF protein was purified by ion exchange chromatography and Ni-affinity chromatography under denaturing conditions in 6 M urea and 20 mM mercaptoethanol. The yield was excellent: 83.5 mg purified 765EGF per liter of culture.

The Ni-purified protein at 2 mg/ml or less in the Ni elution buffer was refolded by slow addition with stirring to 10 volumes of refold buffer, which is 1.6 M urea, 20% 190 proof ethanol, 0.5 M NaCl, 0.1 M glycine, 0.5 mM oxdiized glutathione, 4 mM reduced glutathione, pH 9.6. It was incubated overnight at room temperature.

The refolded protein was acidified to pH 4.5 and then purified at pH 4.5 by cation exchange chromatography.

The refolded protein was subjected to ESI-TOF mass spectrometry. The mass was 85% 8282, which is exactly the predicted mass for the protein with all of the 6 cysteines in disulfides, and 15% 8151, which is the predicted mass of the fully oxidized protein with the initiator methionine removed.

Example 9

765EGF-Bendamustine Conjugate

Native EGF has only two available amino groups (1 lysine side chain and the amino terminus amine). 765EGF has 5 additional lysine side chains, giving it 7 amino groups. We attempted to conjugate to 765EGF the carboxyl-containing cancer chemotherapy drug be bendamustine, whose structure is shown below.

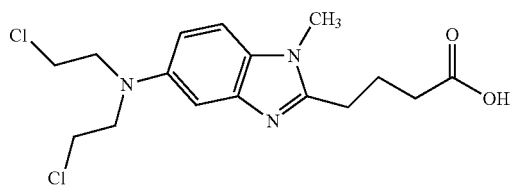 [SMILES: Cn1c(CCCC(=O)O)nc2cc(N(CCCl)CCCl)ccc21]

With reaction with EDC, a direct amide bond is formed between carboxyls and amino groups.

Purified and refolded 765EGF was dialyzed against pH 7.3 conjugation buffer (6 M urea, 10 mM NaCl, 25 mM sodium phosphate, pH 7.3). The dialyzed protein was 34 ml at 1.15 mg/ml.

Bendamustine was dissolved at 20 mg/ml in pH 6.3 conjugation buffer (5.5 ml; 6 M urea, 10 mM NaCl, 25 mM sodium phosphate, pH 6.3). The pH was 4.1. 180 ul of 2 M NaOH was added, which made the pH about 6.7.

EDC was dissolved 60 mg/ml immediately before use. Then 4.25 ml of 60 mg/ml EDC and 4.25 ml 20 mg/ml bendamustine were mixed, and incubated about 30 seconds. Then this mixture was added to the 34 ml of 1.15 mg/ml EGF.

This was incubated overnight at room temperature, then pH adjusted to pH 2.5, then dialyzed against 10 mM HCl. The conjugate was stored at −20 degrees C.

Figure 4:
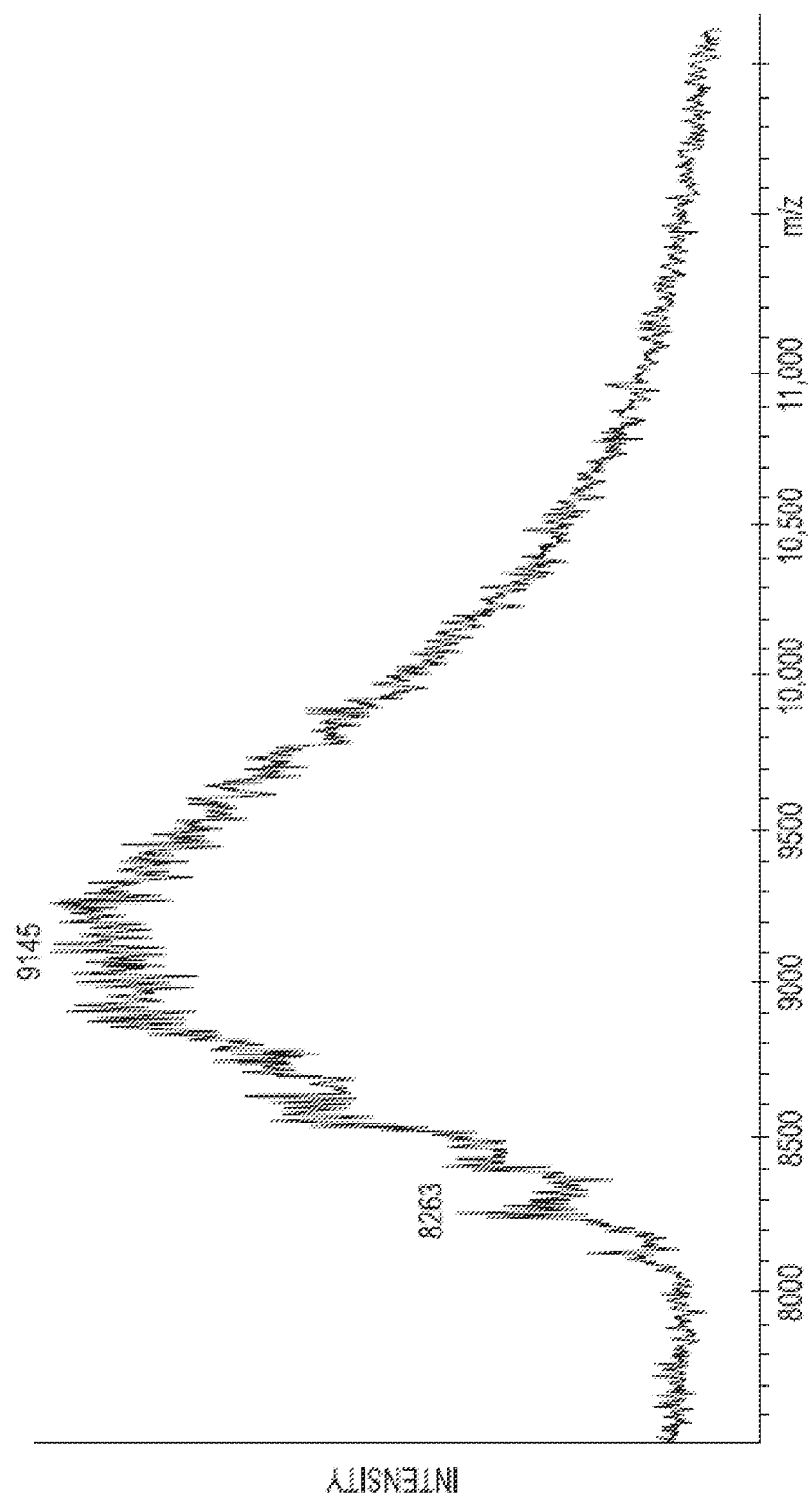
FIG. 4 shows a matrix-assisted laser desorption time of flight (MALDI-TOF) mass spectrum of 765EGF-bendamustine.

The molecular weight of the conjugate was determined by matrix assisted laser desorption (MALDI) mass spectrometry as a broad peak with an average molecular weight of 9145 (FIG. 4). The unconjugated 765EGF has a molecular weight of 8282. Each bendamustine added would add 340 mass after losing one water molecule for the conjugation, so this is 2.5 bendamustine per protein. 765EGF has 7 amino groups available for conjugation (6 lysines and the amino terminus). So an average of 2.5 of the 7 are conjugated. The mass spectrum shows smaller amounts of mass species out to about 10,500. The predicted mass of the species with all 7 amino groups having a bendamustine conjugated would be 10,662. The mass spectrum of the conjugate has almost no specific mass peaks that stand out, suggesting that the product has many variations and cross reactions, rather than being a simple mixture with 1, 2, 3, 4, 5, 6, or 7 unmodified bendamustine groups covalently attached to otherwise unmodified 765EGF protein.

The conjugate was also run on reducing SDS-PAGE (Data not shown). More than 90% of the material ran as 10 kDa monomer. Less than 10% appeared as ~20 kDa dimer.

Example 10

Cytotoxic Activity of 765EGF-Bendamustine

Figure 5:
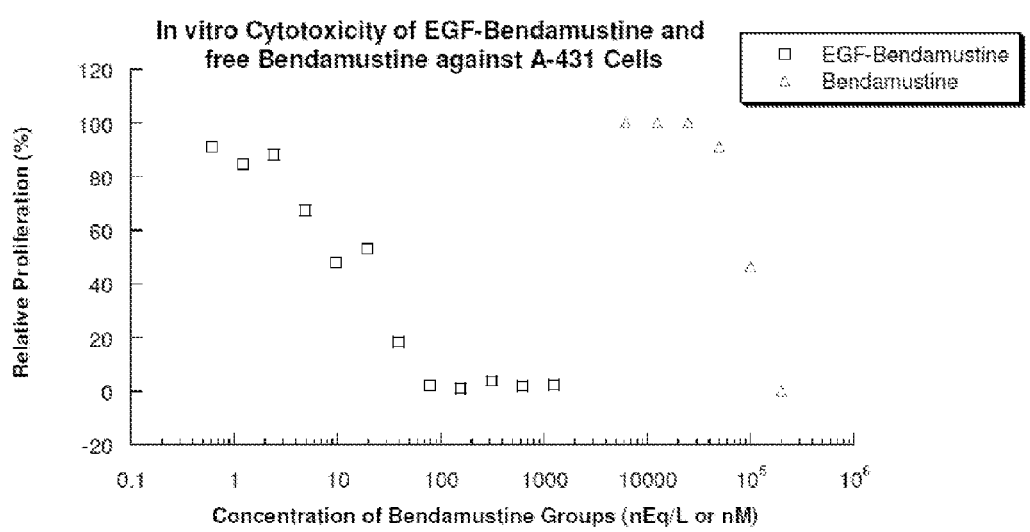
FIG. 5 shows a plot of in vitro proliferation inhibition with A-431 cells by both 765EGF-bendamustine and free bendamustine.
Figure 6:
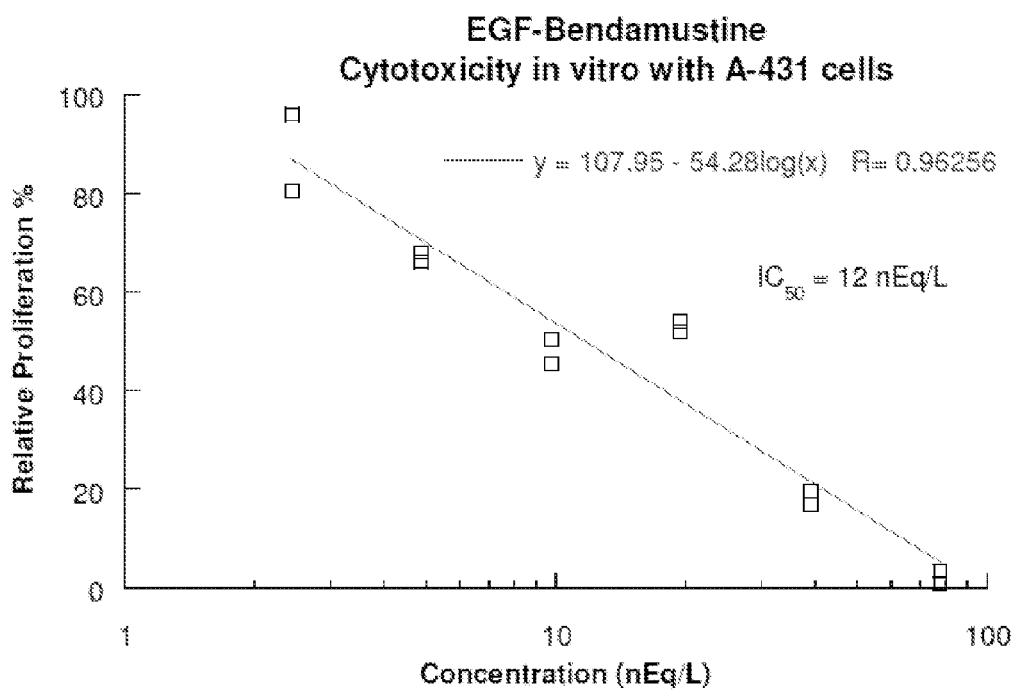
FIG. 6 is a plot of in vitro proliferation inhibition by 765EGF-bendamustine of A-431 cells on which the $IC_{50}$ of 765EGF-bendamustine is calculated.

A-431 human epithelial carcinoma cells were seeded at 5,000 cells per well in 96-well plates and grown for 1 day. A-431 cells have abundant EGF receptors. After 1 day growth, free bendamustine and 765EGF-bendamustine were added to the plate at concentrations ranging from 200 microMolar bendamstine to 6 nM and from 20 microEq/L 765EGF-bendamustine down to 0.6 nM. The plates were incubated with drug at 37 degrees C. under a humidified 5% $CO_2$ atmosphere for 4 days, and then DOJINDO cell counting kit-8 reagent was added to wells to read proliferation. The plates were read according to manufacturer's instruction. The relative proliferation of the cells with both free bendamustine and EGF-bendamustine is shown in FIG. 5. There was a huge difference between free bendamustine and EGF-bendamustine. Free bendamustine only inhibited proliferation at concentrations above about 10 micromolar and had an $IC_{50}$ of about 90 micromolar. EGF-bendamustine had an $IC_{50}$ of 12 nanoEquilavents/L (FIG. 6). The difference in effectiveness was more than 1000-fold expressed in terms of the concentration of bendamustine groups.

Example 11

Tumor Xenograft Treatment In Vivo with 765EGF-Bendamustine

A-431 cells were grown and harvested, and resuspended in media. The cells were counted, and then promptly centrifuged and resuspended in PBS at approximately 7 million cells per ml, and then mixed with an equal volume of matrigel on ice. 100 ul containing 3.5 million cells was injected intradermally in the flank in each mouse. Mice were monitored for tumor growth. Tumor volume was calculated as $(length \times width^2)/2$. When tumors reached 100 mm3, treatment was initiated. Mice were treated on days 0, 7, and 14. Tumor size was measured every 3 or 4 days. Mice received either saline only (dose 0) or EGF-bendamustine at 50, 200, 800, or 3200 picoEquivalents per gram body weight by intraperitoneal injection, or 200 picoEquivalents per gram by intravenous tail vein injection. The drug was at 0.82 mg/ml protein, using a protein molecular weight of 8282 and 2.5 bendamustine groups per protein, this was 250 nanoEquivalents per ml. This was diluted in 2 mM HCl, 150 mM NaCl for injection. A volume of 300 ul was injected for IP injections and 100 ul for IV injections.

Figure 7:
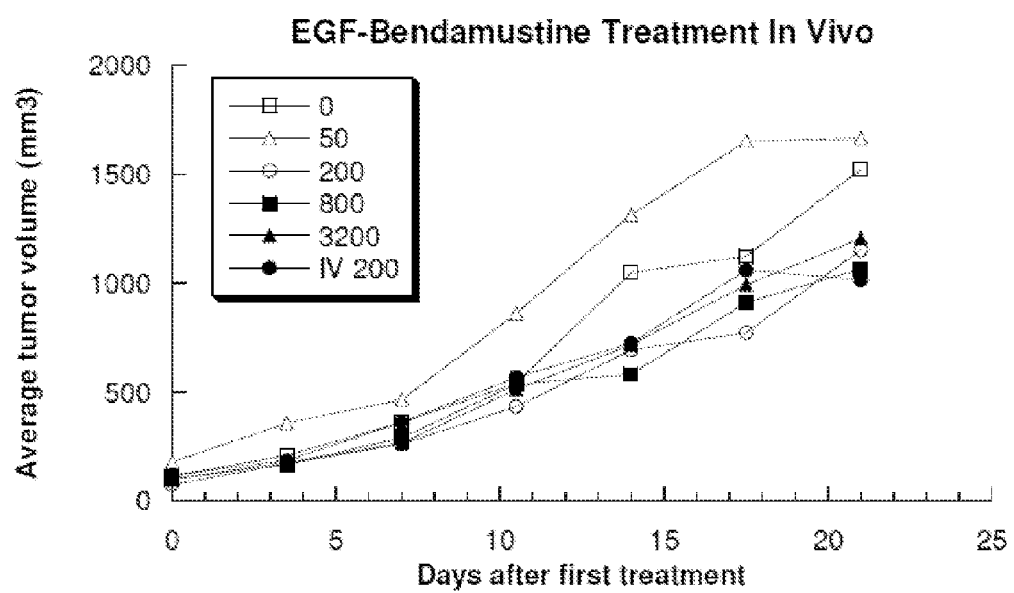
FIG. 7 is a plot of xenograft tumor growth versus time after treatment for the various treatment groups in mice with A-431 xenografts and receiving 765EGF-bendamustine treatment.

Results:

A graph of average tumor volume for the different treatment groups versus time is shown in FIG. 7. All of the treatment groups receiving a dose of 200 pEq/g or greater had reduced tumor growth as compared to the untreated control and the group receiving the smallest dose of 50 pEq/g.

Figure 8:
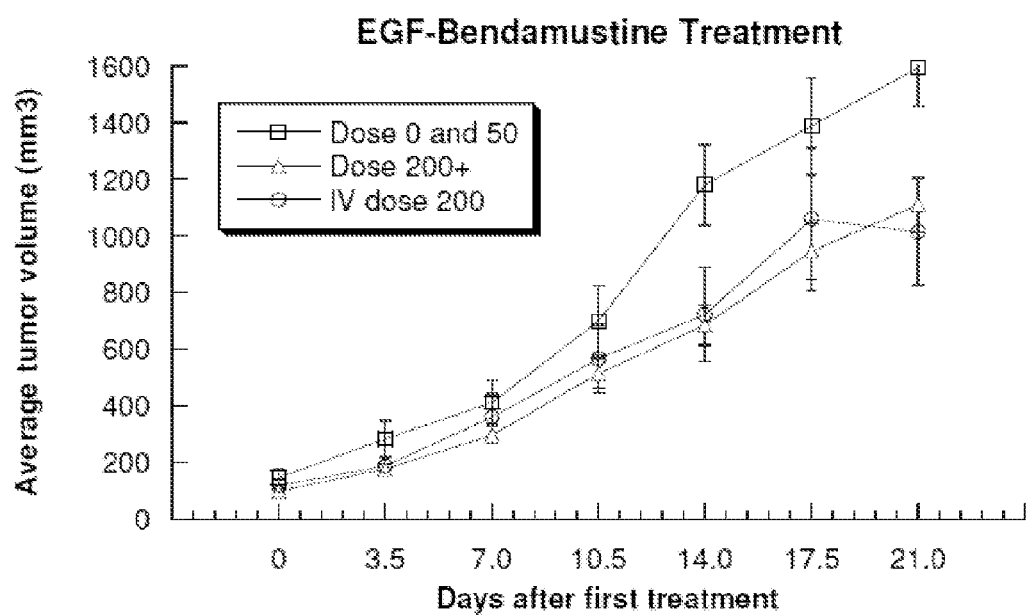
FIG. 8 is a plot of xenograft tumor growth in the 765EGF-bendamustine study with pooled data for the 0 and 50 pEq/g groups, the 200 or more pE/g groups, and the IV 200 pEq/g group.

FIG. 8 shows tumor growth (a) pooled for the groups receiving a dose of 0 or 50 pEq/g, (b) pooled for the groups receiving a dose of 200 pEq/g or higher, and (c) the group receiving an IV dose of 200 pEq/g. At days 14 and beyond, both the 200+ and the IV200 groups were significantly different from the pooled 0+50 group (p=0.05 significance level).

Five mice were cured in the study. That is, their tumors became undetectable and remained so to 50 days after treatment dose 1. Three of ten in the IV200 group were cured, and 1 of 8 receiving the IP dose of 200, and 1 of 7 receiving the IP dose of 800. This is summarized in Table 1. Thus, it appeared that IV administration was more effective than intraperitoneal, although the difference was not statistically significant.

Tumor size and tumor growth delay, was significantly different between mice receiving a dose of 200 pEq/g or higher versus those receiving 50 pEq/g or lower, and between the mice receiving the IV 200 pEq/g dose and the mice receiving 50 pEq/g or lower.

TABLE 1

| dose (pEq/g) | Required more than 26 days to reach 1200 mm³ tumor volume | Required more than 34 days to reach 1200 mm³ tumor volume | Never reached 1200 mm³ tumor volume | 14-day average tumor volume (standard error) | Average[1] days to reach 1200 mm³ (standard error) |
|---|---|---|---|---|---|
| 0 | 0/6 | 0/6 | 0/6 | 1048 (217) | 19.7 (2.32) |
| 50 | 1/6 | 1/6 | 0/6 | 1313 (186) | 18.7 (4.73) |
| 200 | 3/8 | 1/8 | 1/8 | 693 (172) | 26.8 (5.52) |
| 800 | 3/7 | 1/7 | 1/7 | 580 (124) | 29.6 (3.01) |
| 3200 | 4/10 | 1/10 | 0/10 | 714 (111) | 25.3 (3.28) |
| IV 200 | 5/10 (a) | 5/10 (e) | 3/10 | 722 (166)) (c) | 36.5 (6.96) (f) |
| 0 and 50 | 1/12 (a, b) | 1/12 (e) | 0/12 | 1180 (141) (c, d) | 19.2 (2.52) (f, g) |
| 200 or more | 15/35 (b) | 8/35 | 5/35 | 685 (71)(d) | 29.69 (2.795) (g) |

([1]For mice whose tumors never reached 1200 mm³, a value of 62 days was used. a, b, c, d, e, f, and g: cells with the same letter are significantly different from each other, p < 0.05).

Conclusion:

765EGF-bendamustine successfully treated mouse xenografts with A-431, a cell line that has EGF receptors. This cell line was almost completely insensitive to free bendamustine. Thus, conjugation of chemotherapy agents to EGF and EGF fusion proteins is a successful way to target tumor cells expressing EGF receptors.

Example 12

765TNFa Fusion Protein

A plasmid encoding the soluble form of tumor necrosis factor alpha (TNFa) in a fusion protein with the SEQ ID NO:1 leader sequence was synthesized by DNA2.0 (Menlo Park, Calif., USA). The codons were optimized for *E. coli*. The coding sequence was under the expression control of a T7 promoter. The encoded protein is called 765TNFa (SEQ ID NO:17).

*E. coli* BL21(DE3) was transformed with the plasmid, and the transformant was grown in LB medium with 50 ug/ml kanamycin. The culture was induced with 0.4 mM IPTG when it reached an O.D. 600 nm of 0.6. Culture in the amount of 400 ml was grown in each of two 2 L baffled flasks with shaking at 37° C.

Cells were harvested and broken by lysozyme treatment and sonication. Broken cells were centrifuged to remove insoluble debris. 765TNFa protein was purified from the supernatant (soluble fraction) by Nickel affinity chromatography. Fifty mg of purified 765TNFa was obtained from 800 ml of culture. The purified 765TNFa was pure by SDS-PAGE with the predicted mass of 19 kDa (data not shown).

From a fermentor culture, 99 mg of purified 765TNFa was obtained per liter of culture. These yields are excellent.

Activity Assay.

L929 cells were plated at 10,000 cells per well in two 96-well plates in their recommended growth medium with 2% fetal bovine serum. They were grown for 2 days at 37° C. in a 5% $CO_2$ humidified atmosphere. In one plate, after the 2 days incubation 1 ug/ml final concentration actinomycin D was added; in the other plate no actinomycin D was added. 765TNFa was then added at a range of concentrations. Plates were incubated 24 hours more. Then cell viability was quantified with DOJINDO cell counting kit-8 according to manufacturer's instructions. In plates with 1 ug/ml actinomycin, the 765TNFa had an $IC_{50}$ for killing the cells of less than 79 pg/ml. With no actinomycin, the $IC_{50}$ was about 70 ng/ml. These are even lower $IC_{50}$s than are reported in the literature for TNF-alpha. So 765TNFa purified as described is active, possibly more active than wild type TNF-alpha.

SEQUENCES

SEQ ID NO: 1

MVKGKHHHHHHNGKGKSK (765IGF)

SEQ ID NO: 2

MVKGKHHHHH HNGKGKSKGP RTLCGAELVD ALQFVCGDRG FYFNKPTGYG SSSRRAPQTG

IVDECCFRSC DLRRLEMYCA PLKPAKSA (human IGF-1)

SEQ ID NO: 3

GPETLCGAEL VDALQFVCGD RGFYFNKPTG YGSSSRRAPQ TGIVDECCFR SCDLRRLEMY

CAPLKPAKSA (IGF132)

SEQ ID NO: 4

FVNQHLCGSHLVEALYL VCGDRG FYFNKPTGYG SSSRRAPQTG IVDECCFRSCDLRR

LEMYCAPLKPAKSA (long-R3-IGF)

SEQ ID NO: 5

MFPAMPLSSLFVN GPRTL CGALVDALQ FVCGDRGFYF NKPTGYGSSS RRAPQTGIVD

ECCFRSCDLR RLEMYCAPLK PAKSEA (R3-IGF)

SEQ ID NO: 6

GPRTLCGAELVD ALQFVCGDRG FYFNKPTGYG SSSRRAPQTG

IVDECCFRSC DLRRLEMYCA PLKPAKSA (des(1-3)IGF1)

SEQ ID NO: 7

TLCGAELVD ALQFVCGDRG FYFNKPTGYG SSSRRAPQTG

IVDECCFRSC DLRRLEMYCA PLKPAKSA (765EGF)

SEQ ID NO: 8

MVKGKHHHHHHNGKGKSK

NSDSECPLSH DGYCLHDGVC MYIEALDKYA CNCVVGYIGE RCQYRDLKWW ELR

SEQ ID NO: 9, EGF precursor:

-continued

```
                                                        (SEQ ID NO: 9)
MNSDSECPLS HDGYCLHDGV CMYIEALDKY ACNCVVGYIG ERCQYRDLKW WELR

SEQ ID NO: 10, TGFα precursor
                                                       (SEQ ID NO: 10)
MVPSAGQLAL FALGIVLAAC QALENSTSPL SADPPVAAAV VSHFNDCPDS

HTQFCFHGTC RFLVQEDKPA CVCHSGYVGA RCEHADLLAV VAASQKKQAI

TALVVVSIVA LAVLIITCVL IHCCQVRKHC EWCRALICRH EKPSALLKGR

TACCHSETVV

SEQ ID NO: 11, Amphiregulin precursor:
                                                       (SEQ ID NO: 11)
MRAPLLPPAP VVLSLLILGS GHYAAGLDLN DTYSGKREPF SGDHSADGFE

VTSRSEMSSG SEISPVSEMP SSSEPSSGAD YDYSEEYDNE PQIPGYIVDD

SVRVEQVVKP PQNKTESENT SDKPKRKKKG GKNGKNRRNR KKKNPCNAEF

QNFCIHGECK YIEHLEAVTC KCQQEYFGER CGEKSMKTHS MIDSSLSKIA

LAAIAAFMSA VILTAVAVIT VQLRRQYVRK YEGEAEERKK LRQENGNVHA IA

SEQ ID NO: 12, HD-EGF precursor
                                                       (SEQ ID NO: 12)
MKLLPSVVLK LLLAAVLSAL VTGESLEQLR RGLAAGTSNP DPSTGSTDQL

LRLGGGRDRK VRDLQEADLD LLRVTLSSKP QALATPSKEE HGKRKKKGKG

LGKKRDPCLR KYKDFCIHGE CKYVKELRAP SCICHPGYHG ERCHGLSLPV

ENRLYTYDHT TILAVVAVVL SSVCLLVIVG LLMFRYHRRG GYDVENEEKV

KLGMTNSH

SEQ ID NO: 13, Betacellulin precursor:
                                                       (SEQ ID NO: 13)
MDRAARCSGA SSLPLLLALA LGLVILHCVV ADGNSTRSPE TNGLLCGDPE

ENCAATTTQS KRKGHFSRCP KQYKHYCIKG RCRFVVAEQT PSCVCDEGYI

GARCERVDLF YLRGDRGQIL VICLIAVMVV FIILVIGVCT CCHPLRKRRK

RKKKEEEMET LGKDITPINE DIEETNIA

403IGF
                                                        SEQ ID NO: 14
MTSGHHHHHHSAGVNG FVNQHLCGSHL VEALYLVCGD RGFYFNKPTG YGSSSRRAPQ

TGIVDECCFR SCDLRRLEMY CAPLKPAKSA,

784IGF
                                                        SEQ ID NO: 15
MVKQIESKTAFQEALDAAGDKLVVVDFSATWCGHCKMIKPFFHSLSEKYSNVIFLE

VDVDDSQDVASESEVKSMPTFQFFKKGQKVGEFSGANKEKLEATINELVGSKSGHHHHHH

SAKGGPRTLCGAELVDALQFVCGDRGFYFNKPTGYGSSSRRAPQTGIVDECCFRSCDLRR

LEMYCAPLKPAKSA,

785IGF
                                                        SEQ ID NO: 16
MVKQIESKTAFQEALDAAGDKLVVVDFSATWCGHCKMIKPFFHSLSEKYSNVIFLE

VDVDDSQDVASESEVKSMPTFQFFKKGQKVGEFSGANKEKLEATINELVGSKSGHHHHHH

SAKGFVNQHLCGSHLVEALYLVCGDRGFYFNKPTGYGSSSRRAPQTGIVDECCFRSCDLR

RLEMYCAPLKPAKSA,

765TNFa
                                                        SEQ ID NO: 17
MVKGKHHHHHHNGKGKSK

VRSS SRTPSDKPVA HVVANPQAEG QLQWLNRRAN ALLANGVELR

DNQLVVPSEG LYLIYSQVLF KGQGCPSTHV LLTHTISRIA VSYQTKVNLL
```

-continued

SAIKSPCQRE TPEGAEAKPW YEPIYLGGVF QLEKGDRLSA EINRPDYLDF

AESGQVYFGI IAL,

764IGF

SEQ ID NO: 18

MVKGKHHHHHHNGKGKSKFVNQHLCGSHLVEALYLVCGDRGFYFNKPTGYGSSSRR

APQTGIVDECCFRSCDLRRLEMYCAPLKPAKSA,

All patents, patent documents, and other references cited are incorporated by reference.

---

What is claimed is:

1. A fusion protein comprising either SEQ ID NO:1 or residues 2-18 of SEQ ID NO:1; fused directly to the N-terminus of a cytokine.

2. The fusion protein of claim 1 wherein the cytokine is a ligand to ErbB-1 or IGFR1.

3. The fusion protein of claim 1 wherein the cytokine is tumor necrosis factor-alpha.

4. The fusion protein of claim 3 comprising SEQ ID NO: 17 or residues 2-175 of SEQ ID NO: 17.

5. The fusion protein of claim 1 wherein the cytokine is selected from a group consisting of: SEQ ID NO:3, SEQ ID NO:4, SEQ ID NO:6, SEQ ID NO:7, residues 2-54 of SEQ ID NO:9, residues 40-89 of SEQ ID NO:10, residues 101-184 of SEQ ID NO:11, residues 63-148 of SEQ ID NO:12, and residues 32-111 of SEQ ID NO:13.

6. The fusion protein of claim 5 wherein the cytokine is SEQ ID NO:3, SEQ ID NO:4, SEQ ID NO:6, or SEQ ID NO:7.

7. The fusion protein of claim 5 wherein the cytokine is residues 2-54 of SEQ ID NO:9, residues 40-89 of SEQ ID NO:10, residues 101-184 of SEQ ID NO:11, residues 63-148 of SEQ ID NO:12, or residues 32-111 of SEQ ID NO:13.

8. The fusion protein of claim 5 wherein the fusion protein comprises SEQ ID NO:2 or residues 2-88 of SEQ ID NO:2.

9. The fusion protein of claim 5 wherein the cytokine is residues 2-54 of SEQ ID NO:9.

10. A fusion protein consisting of either SEQ ID NO:1 or residues 2-18 of SEQ ID NO:1 fused to the N terminus of a cytokine selected from the group consisting of SEQ ID NO:3, SEQ ID NO:4, SEQ ID NO:6, SEQ ID NO:7, residues 2-54 of SEQ ID NO:9, residues 40-89 of SEQ ID NO:10, residues 101-184 of SEQ ID NO:11, residues 63-148 of SEQ ID NO:12, or residues 32-111 of SEQ ID NO:13.

11. The fusion protein of claim 10 consisting of SEQ ID NO:2 or residues 2-88 of SEQ ID NO:2.

* * * * *